United States Patent
Johannigman et al.

(10) Patent No.: US 9,539,155 B2
(45) Date of Patent: Jan. 10, 2017

(54) CONTROL SYSTEM FOR PATIENT SUPPORT APPARATUS

(71) Applicant: Hill-Rom Services, Inc., Batesville, IN (US)

(72) Inventors: Nicole Johannigman, Greensburg, IN (US); William A. Morrison, Batesville, IN (US); Douglas A. Seim, Okeana, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 519 days.

(21) Appl. No.: 13/803,608

(22) Filed: Mar. 14, 2013

(65) Prior Publication Data
US 2014/0115784 A1    May 1, 2014

Related U.S. Application Data

(60) Provisional application No. 61/719,239, filed on Oct. 26, 2012.

(51) Int. Cl.
| G06F 19/00 | (2011.01) |
| A61G 7/00 | (2006.01) |
| A61G 7/018 | (2006.01) |

(52) U.S. Cl.
CPC .............. *A61G 7/00* (2013.01); *A61G 7/018* (2013.01); *G06F 19/3418* (2013.01); *A61G 2203/46* (2013.01)

(58) Field of Classification Search
USPC ............................ 700/157; 5/600; 455/456.1
See application file for complete search history.

(56) References Cited

U.S. PATENT DOCUMENTS

| 3,599,199 A | 8/1971 | Bunting |
| 3,643,219 A | 2/1972 | Heimann |
| 3,910,659 A | 10/1975 | Peterson et al. |
| 3,913,153 A | 10/1975 | Adams et al. |
| 3,946,159 A | 3/1976 | Fay |
| 4,183,015 A | 1/1980 | Drew et al. |
| 4,216,462 A | 8/1980 | McGrath et al. |

(Continued)

FOREIGN PATENT DOCUMENTS

| CN | 101668503 B | 9/2013 |
| DE | 10141053 B4 | 1/2006 |

(Continued)

OTHER PUBLICATIONS

Partial European Search Report for Application No. EP 13189571 dated Feb. 6, 2014, 6 pages.

(Continued)

*Primary Examiner* — Kidest Bahta
(74) *Attorney, Agent, or Firm* — Barnes & Thornburg LLP

(57) ABSTRACT

A system includes a patient support apparatus that has one or more therapies. The therapies are optionally available depending on the acuity of the patient. A request for enablement of a therapy is transferred to a service provider for approval and, when approved, the therapy is enabled by the service provider. The patient support apparatus may be in communication with a server that is in communication with multiple patient support apparatuses so that the server is operable to selectively enable therapies on various patient support apparatuses.

20 Claims, 19 Drawing Sheets

(56) References Cited

U.S. PATENT DOCUMENTS

| | | |
|---|---|---|
| 4,237,344 A | 12/1980 | Moore |
| 4,356,475 A | 10/1982 | Neumann et al. |
| 4,410,158 A | 10/1983 | Maffei et al. |
| 4,452,499 A | 6/1984 | Verburg |
| 4,489,454 A | 12/1984 | Thompson |
| 4,539,560 A | 9/1985 | Fleck et al. |
| 4,557,453 A | 12/1985 | McCloskey |
| 4,584,989 A | 4/1986 | Stith |
| 4,601,064 A | 7/1986 | Shipley |
| 4,607,897 A | 8/1986 | Schwartz et al. |
| 4,638,313 A | 1/1987 | Sherwood et al. |
| 4,640,485 A | 2/1987 | Day et al. |
| 4,680,790 A | 7/1987 | Packard et al. |
| 4,687,167 A | 8/1987 | Skalka et al. |
| 4,708,312 A | 11/1987 | Rohr |
| 4,715,385 A | 12/1987 | Cudahy et al. |
| 4,724,555 A | 2/1988 | Poehner et al. |
| 4,738,369 A | 4/1988 | Desjardins |
| 4,747,172 A | 5/1988 | Hohol et al. |
| 4,756,706 A | 7/1988 | Kerns et al. |
| 4,768,241 A | 9/1988 | Beney |
| 4,783,036 A | 11/1988 | Vossoughi |
| 4,800,384 A | 1/1989 | Snijders |
| 4,835,372 A | 5/1989 | Gombrich et al. |
| 4,836,478 A | 6/1989 | Sweere |
| 4,848,710 A | 7/1989 | Newman et al. |
| 4,852,500 A | 8/1989 | Ryburg et al. |
| 4,857,713 A | 8/1989 | Brown et al. |
| 4,872,679 A | 10/1989 | Bohaski et al. |
| 4,890,856 A | 1/1990 | Mursch et al. |
| 4,934,933 A | 6/1990 | Fuchs |
| 4,945,592 A | 8/1990 | Sims et al. |
| 4,967,195 A | 10/1990 | Shipley et al. |
| 4,981,139 A | 1/1991 | Pfohl |
| 4,993,683 A | 2/1991 | Kreuzer et al. |
| 5,023,967 A | 6/1991 | Ferrand et al. |
| 5,036,852 A | 8/1991 | Leishman |
| 5,065,154 A | 11/1991 | Kaiser et al. |
| 5,072,906 A | 12/1991 | Foster et al. |
| 5,077,843 A | 1/1992 | Dale et al. |
| 5,108,063 A | 4/1992 | Koerber, Sr. et al. |
| 5,117,521 A | 6/1992 | Foster et al. |
| 5,177,616 A | 1/1993 | Riday |
| 5,187,641 A | 2/1993 | Muskatello et al. |
| 5,246,240 A | 9/1993 | Romich et al. |
| 5,272,318 A | 12/1993 | Gorman |
| 5,274,311 A | 12/1993 | Littlejohn et al. |
| 5,276,813 A | 1/1994 | Elliott et al. |
| 5,279,010 A | 1/1994 | Ferrand et al. |
| 5,283,781 A | 2/1994 | Buda et al. |
| 5,284,255 A | 2/1994 | Foster et al. |
| 5,291,399 A | 3/1994 | Chaco et al. |
| 5,319,816 A | 6/1994 | Ruehl et al. |
| 5,330,415 A | 7/1994 | Storti et al. |
| 5,335,651 A | 8/1994 | Foster et al. |
| 5,337,845 A | 8/1994 | Foster et al. |
| 5,357,396 A | 10/1994 | Alm |
| 5,361,755 A | 11/1994 | Schraag et al. |
| 5,362,021 A | 11/1994 | Phillips |
| 5,375,604 A | 12/1994 | Kelly et al. |
| 5,377,371 A | 1/1995 | Foster et al. |
| 5,396,673 A | 3/1995 | Foster |
| 5,398,359 A | 3/1995 | Foster |
| 5,400,991 A | 3/1995 | Werner et al. |
| 5,407,163 A | 4/1995 | Kramer et al. |
| 5,416,695 A | 5/1995 | Stutman et al. |
| 5,417,222 A | 5/1995 | Dempsey et al. |
| 5,455,975 A | 10/1995 | Foster et al. |
| 5,457,831 A | 10/1995 | Foster et al. |
| 5,473,536 A | 12/1995 | Wimmer et al. |
| 5,473,997 A | 12/1995 | Solomon et al. |
| 5,494,051 A | 2/1996 | Schneider et al. |
| 5,497,766 A | 3/1996 | Foster et al. |
| 5,502,480 A | 3/1996 | Kuga et al. |
| 5,513,406 A | 5/1996 | Foster et al. |
| 5,527,289 A | 6/1996 | Foster et al. |
| 5,536,084 A | 7/1996 | Curtis et al. |
| 5,537,459 A | 7/1996 | Price et al. |
| 5,542,138 A | 8/1996 | Williams et al. |
| 5,544,649 A | 8/1996 | David et al. |
| 5,556,065 A | 9/1996 | Wadley et al. |
| 5,561,412 A | 10/1996 | Novak et al. |
| 5,562,091 A | 10/1996 | Foster et al. |
| 5,579,001 A | 11/1996 | Dempsey et al. |
| 5,579,775 A | 12/1996 | Dempsey et al. |
| 5,600,311 A | 2/1997 | Rice et al. |
| 5,618,090 A | 4/1997 | Montague et al. |
| 5,623,925 A | 4/1997 | Swenson et al. |
| 5,630,566 A | 5/1997 | Case et al. |
| 5,640,953 A | 6/1997 | Bishop et al. |
| 5,647,491 A | 7/1997 | Foster et al. |
| 5,651,775 A | 7/1997 | Walker et al. |
| 5,664,270 A | 9/1997 | Bell et al. |
| 5,687,717 A | 11/1997 | Halpern et al. |
| 5,699,038 A | 12/1997 | Ulrich et al. |
| 5,712,482 A | 1/1998 | Gaiser et al. |
| 5,715,138 A | 2/1998 | Choi |
| 5,732,401 A | 3/1998 | Conway et al. |
| 5,732,712 A | 3/1998 | Adair et al. |
| 5,738,102 A | 4/1998 | Lemelson |
| 5,738,316 A | 4/1998 | Sweere et al. |
| 5,743,503 A | 4/1998 | Voeller et al. |
| 5,749,374 A | 5/1998 | Schneider et al. |
| 5,752,917 A | 5/1998 | Fuchs |
| 5,769,440 A | 6/1998 | Jones |
| 5,771,511 A | 6/1998 | Kummer et al. |
| 5,772,585 A | 6/1998 | Lavin et al. |
| 5,772,599 A | 6/1998 | Nevo et al. |
| 5,788,851 A | 8/1998 | Kenley et al. |
| 5,791,263 A | 8/1998 | Watt et al. |
| 5,799,917 A | 9/1998 | Li |
| 5,820,623 A | 10/1998 | Ng et al. |
| 5,822,544 A | 10/1998 | Chaco et al. |
| 5,826,846 A | 10/1998 | Buccieri et al. |
| 5,831,816 A | 11/1998 | Johns et al. |
| 5,838,223 A | 11/1998 | Gallant et al. |
| 5,841,373 A | 11/1998 | Mason |
| 5,842,672 A | 12/1998 | Sweere et al. |
| 5,842,976 A | 12/1998 | Williamson |
| 5,867,821 A | 2/1999 | Ballantyne et al. |
| 5,876,008 A | 3/1999 | Sweere et al. |
| 5,883,370 A | 3/1999 | Walker et al. |
| 5,889,568 A | 3/1999 | Seraphim et al. |
| 5,895,354 A | 4/1999 | Simmons |
| 5,895,571 A | 4/1999 | Utterberg |
| 5,898,961 A | 5/1999 | Ambach et al. |
| 5,903,211 A | 5/1999 | Flego et al. |
| 5,907,291 A | 5/1999 | Chen et al. |
| 5,918,328 A | 7/1999 | Ramsey |
| 5,918,331 A | 7/1999 | Hall et al. |
| 5,918,841 A | 7/1999 | Sweere et al. |
| 5,924,665 A | 7/1999 | Sweere et al. |
| 5,944,659 A | 8/1999 | Flach et al. |
| 5,947,429 A | 9/1999 | Sweere et al. |
| 5,957,838 A | 9/1999 | Rantala |
| 5,960,085 A | 9/1999 | De La Huerga |
| 5,961,448 A | 10/1999 | Swenson et al. |
| 5,966,760 A | 10/1999 | Gallant et al. |
| 5,973,598 A | 10/1999 | Beigel |
| 5,975,081 A | 11/1999 | Hood et al. |
| 5,978,211 A | 11/1999 | Hong |
| 5,991,947 A | 11/1999 | Lavin et al. |
| 5,992,809 A | 11/1999 | Sweere et al. |
| 5,993,006 A | 11/1999 | Takeuchi et al. |
| 5,997,147 A | 12/1999 | Tatoian et al. |
| 6,001,057 A | 12/1999 | Bongiovanni et al. |
| 6,008,598 A | 12/1999 | Luff et al. |
| 6,011,701 A | 1/2000 | Kopp et al. |
| 6,012,693 A | 1/2000 | Voeller et al. |
| 6,015,120 A | 1/2000 | Sweere et al. |
| 6,019,332 A | 2/2000 | Sweere et al. |
| 6,026,318 A | 2/2000 | Bernstein et al. |
| 6,027,247 A | 2/2000 | Tachi et al. |
| 6,061,104 A | 5/2000 | Evanicky et al. |

(56) References Cited

U.S. PATENT DOCUMENTS

| | | | |
|---|---|---|---|
| 6,064,373 A | 5/2000 | Ditzik |
| 6,065,732 A | 5/2000 | Cho |
| 6,073,285 A | 6/2000 | Ambach et al. |
| 6,089,518 A | 7/2000 | Nilsson |
| 6,102,476 A | 8/2000 | May et al. |
| 6,102,855 A | 8/2000 | Kehr et al. |
| 6,104,443 A | 8/2000 | Adcock et al. |
| 6,112,182 A | 8/2000 | Akers et al. |
| 6,125,350 A | 9/2000 | Dirbas et al. |
| 6,134,103 A | 10/2000 | Ghanma |
| 6,143,181 A | 11/2000 | Falkvall et al. |
| 6,144,848 A | 11/2000 | Walsh et al. |
| 6,146,523 A | 11/2000 | Kenley et al. |
| 6,147,592 A | 11/2000 | Ulrich et al. |
| 6,150,942 A | 11/2000 | O'Brien |
| 6,155,603 A | 12/2000 | Fox |
| 6,155,975 A | 12/2000 | Urich et al. |
| 6,168,250 B1 | 1/2001 | Rogov |
| 6,170,102 B1 | 1/2001 | Kreuzer |
| 6,175,779 B1 | 1/2001 | Barrett |
| 6,175,977 B1 | 1/2001 | Schumacher et al. |
| 6,176,456 B1 | 1/2001 | Wisniewski |
| 6,179,260 B1 | 1/2001 | Ohanian |
| 6,183,417 B1 | 2/2001 | Geheb et al. |
| 6,189,842 B1 | 2/2001 | Bergeron Gull et al. |
| 6,202,360 B1 | 3/2001 | Rattner et al. |
| 6,202,923 B1 | 3/2001 | Boyer et al. |
| 6,205,601 B1 | 3/2001 | Nessmann et al. |
| 6,208,250 B1 | 3/2001 | Dixon et al. |
| 6,219,587 B1 | 4/2001 | Ahlin et al. |
| 6,234,172 B1 | 5/2001 | Ausbourne et al. |
| 6,246,573 B1 | 6/2001 | Khan et al. |
| 6,260,761 B1 | 7/2001 | Peoples, Jr. |
| 6,320,510 B2 | 11/2001 | Menkedick et al. |
| 6,352,504 B1 | 3/2002 | Ise et al. |
| 6,396,224 B1 | 5/2002 | Luff et al. |
| 6,481,688 B1 | 11/2002 | Welling et al. |
| 6,486,792 B1 | 11/2002 | Moster et al. |
| 6,493,568 B1 | 12/2002 | Bell et al. |
| 6,510,049 B2 | 1/2003 | Rosen |
| 6,560,492 B2 | 5/2003 | Borders |
| 6,560,798 B2 | 5/2003 | Welling et al. |
| 6,591,239 B1 | 7/2003 | McCall et al. |
| 6,616,606 B1 | 9/2003 | Petersen et al. |
| 6,640,363 B1 | 11/2003 | Pattee et al. |
| 6,642,836 B1 | 11/2003 | Wang et al. |
| 6,759,959 B2 | 7/2004 | Wildman |
| 6,761,344 B2 | 7/2004 | Welling et al. |
| 6,781,517 B2 | 8/2004 | Moster et al. |
| 6,785,922 B2 | 9/2004 | Bretschger et al. |
| 6,791,460 B2 | 9/2004 | Dixon et al. |
| 6,829,796 B2 | 12/2004 | Salvatini et al. |
| 6,840,117 B2 | 1/2005 | Hubbard, Jr. |
| 6,876,303 B2 | 4/2005 | Reeder et al. |
| 6,897,780 B2 | 5/2005 | Ulrich et al. |
| 6,907,630 B2 | 6/2005 | Treon |
| 6,911,916 B1 | 6/2005 | Wang et al. |
| 6,915,538 B2 | 7/2005 | Treon |
| 6,924,441 B1 | 8/2005 | Mobley et al. |
| 6,943,663 B2 | 9/2005 | Wang et al. |
| 6,944,896 B2 | 9/2005 | Treon |
| 6,947,411 B2* | 9/2005 | Parker ............ H04N 21/25891 |
| | | 348/E7.081 |
| 6,957,458 B2 | 10/2005 | Nagaoka et al. |
| 6,972,683 B2 | 12/2005 | Lestienne et al. |
| 6,980,111 B2 | 12/2005 | Nolte |
| 7,010,369 B2 | 3/2006 | Borders et al. |
| 7,017,208 B2 | 3/2006 | Weismiller et al. |
| 7,032,522 B2 | 4/2006 | George et al. |
| 7,038,588 B2 | 5/2006 | Boone et al. |
| 7,103,419 B2 | 9/2006 | Engleson et al. |
| 7,119,688 B2 | 10/2006 | Wildman |
| 7,154,307 B2 | 12/2006 | Pradhan et al. |
| 7,154,397 B2 | 12/2006 | Zerhusen et al. |
| 7,174,678 B2 | 2/2007 | Gallant |
| 7,176,391 B2 | 2/2007 | Metz et al. |
| 7,197,148 B2 | 3/2007 | Nourse et al. |
| 7,213,279 B2 | 5/2007 | Weismiller et al. |
| 7,237,287 B2* | 7/2007 | Weismiller ............ A61G 7/002 |
| | | 318/16 |
| 7,242,308 B2 | 7/2007 | Ulrich et al. |
| 7,310,839 B2 | 12/2007 | Salvatini et al. |
| 7,335,839 B2 | 2/2008 | Metz et al. |
| 7,346,945 B2 | 3/2008 | Phillips et al. |
| 7,399,205 B2 | 7/2008 | McNeely et al. |
| 7,421,474 B2 | 9/2008 | Motoyama et al. |
| 7,426,760 B2 | 9/2008 | Vrzalik |
| 7,443,302 B2 | 10/2008 | Reeder et al. |
| 7,451,506 B2 | 11/2008 | Kummer et al. |
| 7,461,009 B1 | 12/2008 | Haulk et al. |
| 7,467,093 B1 | 12/2008 | Newton et al. |
| 7,480,951 B2* | 1/2009 | Weismiller ............ A61G 7/002 |
| | | 5/600 |
| 7,506,390 B2 | 3/2009 | Dixon et al. |
| 7,538,659 B2 | 5/2009 | Ulrich et al. |
| 7,568,246 B2 | 8/2009 | Weismiller et al. |
| 7,679,520 B2 | 3/2010 | Zerhusen et al. |
| 7,730,562 B2 | 6/2010 | Hornbach et al. |
| 7,757,318 B2 | 7/2010 | Poulos et al. |
| 7,784,128 B2 | 8/2010 | Kramer |
| 7,805,785 B2 | 10/2010 | Rawls-Meehan |
| 7,827,632 B2 | 11/2010 | Vrzalik |
| 7,834,768 B2 | 11/2010 | Dixon et al. |
| 7,860,726 B2 | 12/2010 | Connely, III et al. |
| 7,911,349 B2 | 3/2011 | Zerhusen et al. |
| 7,945,451 B2 | 5/2011 | Cosentino et al. |
| 7,971,300 B2 | 7/2011 | Wilker, Jr. |
| 7,978,084 B2 | 7/2011 | Dixon et al. |
| 7,986,242 B2 | 7/2011 | Dixon et al. |
| 8,026,821 B2 | 9/2011 | Reeder et al. |
| 8,032,078 B1 | 10/2011 | Donich et al. |
| 8,032,263 B2 | 10/2011 | Rawls-Meehan |
| 8,032,960 B2 | 10/2011 | Rawls-Meehan |
| 8,065,764 B2 | 11/2011 | Kramer |
| 8,069,512 B2 | 12/2011 | Rawls-Meehan |
| 8,091,162 B2 | 1/2012 | Wurdeman |
| 8,111,165 B2 | 2/2012 | Ortega et al. |
| 8,112,836 B2 | 2/2012 | Tesar et al. |
| 8,121,856 B2 | 2/2012 | Huster et al. |
| 8,125,318 B2 | 2/2012 | Heimbrock et al. |
| 8,161,826 B1 | 4/2012 | Taylor |
| 8,258,963 B2 | 9/2012 | Dixon et al. |
| 8,258,965 B2 | 9/2012 | Reeder et al. |
| 8,266,742 B2 | 9/2012 | Andrienko |
| 8,280,748 B2 | 10/2012 | Allen et al. |
| 8,314,781 B2 | 11/2012 | Pittenger et al. |
| 8,327,479 B2 | 12/2012 | Wurdeman |
| 8,334,777 B2 | 12/2012 | Wilson et al. |
| 8,334,779 B2 | 12/2012 | Zerhusen et al. |
| 8,344,860 B2 | 1/2013 | Collins, Jr. et al. |
| 8,368,545 B2 | 2/2013 | Zerhusen et al. |
| 8,375,488 B2 | 2/2013 | Rawls-Meehan |
| 8,393,026 B2 | 3/2013 | Dionne et al. |
| 8,400,311 B2 | 3/2013 | Dixon et al. |
| 8,413,274 B2 | 4/2013 | Weismiller et al. |
| 8,416,088 B2 | 4/2013 | Ortega et al. |
| 8,419,650 B2 | 4/2013 | Cosentino et al. |
| 8,419,660 B1 | 4/2013 | Shaw |
| 8,432,287 B2 | 4/2013 | O'Keefe et al. |
| 8,438,038 B2 | 5/2013 | Cosentino et al. |
| 8,438,680 B2 | 5/2013 | Wurdeman |
| 8,461,982 B2 | 6/2013 | Becker et al. |
| 8,464,380 B2 | 6/2013 | Bobey et al. |
| 8,474,072 B2 | 7/2013 | O'Keefe et al. |
| 8,474,076 B2 | 7/2013 | Hornbach |
| 8,487,774 B2 | 7/2013 | Reeder et al. |
| 8,499,385 B2 | 8/2013 | Horitani |
| 8,525,682 B2 | 9/2013 | Dixon et al. |
| 8,533,879 B1 | 9/2013 | Taylor |
| 8,537,008 B2 | 9/2013 | Tallent et al. |
| 8,565,934 B2 | 10/2013 | Rawls-Meehan |
| 8,593,284 B2 | 11/2013 | Tallent et al. |
| 8,616,438 B2 | 12/2013 | Zerhusen et al. |
| 8,618,918 B2 | 12/2013 | Tallent et al. |

(56) References Cited

U.S. PATENT DOCUMENTS

| | | |
|---|---|---|
| 2002/0014951 A1 | 2/2002 | Kramer et al. |
| 2002/0044059 A1 | 4/2002 | Reeder et al. |
| 2002/0053086 A1 | 5/2002 | Vanderpohl, III et al. |
| 2002/0059679 A1 | 5/2002 | Weismiller et al. |
| 2002/0152211 A1 | 10/2002 | Jam |
| 2002/0196150 A1 | 12/2002 | Wildman |
| 2003/0052787 A1 | 3/2003 | Zerhusen et al. |
| 2005/0172405 A1* | 8/2005 | Menkedick ............ A61G 7/018 5/618 |
| 2006/0058587 A1* | 3/2006 | Heimbrock .......... A61B 6/0457 600/300 |
| 2006/0180054 A1 | 8/2006 | George et al. |
| 2006/0260054 A1* | 11/2006 | Lubbers ................ A61G 7/018 5/621 |
| 2007/0120689 A1 | 5/2007 | Zerhusen et al. |
| 2007/0124177 A1 | 5/2007 | Engleson et al. |
| 2007/0180616 A1* | 8/2007 | Newkirk ............... A61G 7/018 5/425 |
| 2007/0210917 A1* | 9/2007 | Collins, Jr. ............ A61B 5/447 340/539.1 |
| 2009/0096615 A1* | 4/2009 | Reeder ................ A61B 5/0002 340/573.4 |
| 2010/0073168 A1 | 3/2010 | Tallent et al. |
| 2010/0154124 A1 | 6/2010 | Zerhusen et al. |
| 2011/0208541 A1* | 8/2011 | Wilson ................... A61G 7/018 705/3 |
| 2011/0234411 A1 | 9/2011 | Harrington et al. |
| 2011/0245979 A1 | 10/2011 | Koch |
| 2012/0004789 A1 | 1/2012 | Wilker, Jr. |
| 2012/0086575 A1 | 4/2012 | Dixon et al. |
| 2012/0137439 A1 | 6/2012 | Heimbrock |
| 2013/0043997 A1 | 2/2013 | Cosentino et al. |

FOREIGN PATENT DOCUMENTS

| | | |
|---|---|---|
| DE | 102010031530 A1 | 1/2012 |
| EP | 0168158 | 1/1986 |
| EP | 0 376 066 | 8/1995 |
| EP | 656183 A2 | 8/2001 |
| EP | 1524759 A2 | 4/2005 |
| EP | 2093724 A2 | 8/2009 |
| EP | 2093988 A2 | 8/2009 |
| EP | 2119421 A1 | 11/2009 |
| EP | 2181685 A2 | 5/2010 |
| EP | 2460503 A2 | 6/2012 |
| EP | 2495708 A2 | 9/2012 |
| EP | 2495711 A2 | 9/2012 |
| EP | 2495712 A2 | 9/2012 |
| EP | 2575263 A1 | 4/2013 |
| EP | 2586413 A2 | 5/2013 |
| EP | 2599435 A1 | 6/2013 |
| GB | 2 218 149 | 11/1989 |
| GB | 2 333 391 | 7/1999 |
| WO | WO 94/13198 | 6/1994 |
| WO | WO 94/22098 | 9/1994 |
| WO | 9705844 A1 | 2/1997 |
| WO | WO 98/02107 | 1/1998 |
| WO | WO 98/08203 | 2/1998 |
| WO | WO 98/29775 | 7/1998 |
| WO | WO 99/42021 | 8/1999 |
| WO | WO 99/52487 | 10/1999 |
| WO | WO 00/03344 | 1/2000 |
| WO | WO 01/57610 | 8/2001 |
| WO | 01/85085 | 11/2001 |
| WO | WO 01/97745 | 12/2001 |
| WO | 2005102242 A1 | 11/2005 |
| WO | 2006046928 A1 | 5/2006 |
| WO | 2010088575 A2 | 8/2010 |
| WO | 2012010588 A1 | 1/2012 |

OTHER PUBLICATIONS

Extended European Search Report for Application No. EP 13189571 dated May 28, 2014, 9 pages.
Pyxis PatientStation . . . Copyrgt. Bedside Computing System by CardinalHealth, http://www.pyxis.com/prodDetails.aspx?pid=55, last accessed Jan. 18, 2007, original date of publication unknown.
Tierney, W., Miller, M., & McDonald, C. (1990). The effect on test ordering of informing physicians of the charges for outpatient diagnostic tests. The New England journal of medicine, 322(21), 1499-1504.
McDonald, C. J., Overhage, J. M., Abernathy, G., Harris, L., Smith, R. N., Terry Hogan, R. N., . . . & Tucker, M. The Regenstrief Medical Record System (RMRS): Physician use for input and output and Web browser based computing.
European Search Report dated Mar. 21, 2011 for EP 10 00 3711, 7 pages.
Partial European Search Report dated Mar. 23, 2011 for EP 10 07 5540, 3 pages.
Partial European Search Report dated Mar. 24, 2011 for EP 10 07 5542, 3 pages.
European Search Report dated Aug. 10, 2011 for EP 10 07 5540, 9 pages.
European Search Report dated Aug. 10, 2011 for EP 10 07 5542, 12 pages.
Extended European Search Report, European Application No. 15202342.0, completed Apr. 12, 2016, (9 pages).

* cited by examiner

CONTROL SYSTEM FOR PATIENT SUPPORT APPARATUS

This application claims priority under 35 U.S.C. §119(e) to U.S. Provisional Application Ser. No. 61/719,239, filed Oct. 26, 2012, which is expressly incorporated by reference herein.

BACKGROUND

The present disclosure relates to a patient support apparatus, and particularly, to a patient support apparatus and a control system configured to control various functions of the patient support apparatus. More particularly, the present disclosure relates to a control system configured to control interaction between caregivers, patients, and service providers regarding the use and implementation of features included in the patient support apparatus.

It is known to provide patient support apparatuses that are configured to provide various features and therapies which caregivers and patients may desire to use. The cost of a patient support apparatus having many features and therapies available may be significant to the caregiver or patient. As a result, caregivers and patients may rent such patient support apparatuses for the limited times such features and therapies are needed. As a result, scheduling, shipping, and service of the patient support apparatus must be managed and coordinated.

It is also known to adjust features and therapies of the patient support apparatuses in the event maintenance or patient care necessitates such changes. When such an adjustment is needed, service providers often send a technician to the patient support apparatus to make adjustments. In the event of a maintenance event, the technician may enable alternative therapies or features until the desired feature or therapy is repaired. In the event of patient care calls for a change, the technician may enable the desired feature or therapy or provide an alternate therapy where patient care may be maximized as a result.

It is also known that certain therapies and features may not be covered by a patient's insurance provider. As a result, a caregiver may enable a feature or therapy which is not reimbursable by the insurance. Such cost may not be readily chargeable back to the patient and costs to the caregiver and patient are not optimized.

It is also know that billing of patients and caregivers for the time features and therapies are actually in use is inaccurate due to the limited availability of information. Caregivers and patients may be billed from the time the patient support apparatus is delivered from the service provider to the time the patient support apparatus is returned to the service provided. Caregivers may also be billed from the time a technician enables a feature or therapy to the time patient support apparatus is reconfigured for another patient. As a result, billing is inaccurate and inefficient.

SUMMARY

The present application discloses one or more of the features recited in the appended claims and/or the following features which, alone or in any combination, may comprise patentable subject matter:

According to a first aspect of the present disclosure, a system comprises a first patient support apparatus having a plurality of devices that are independently operational and a server spaced apart from the patient support apparatus. Each of the plurality of devices provides a distinct therapy to a patient supported on the patient support apparatus. The patient support apparatus includes a control system operable to enable or disable each independently operational device under software control. The server is in communication with the control system of the first patient support apparatus. The server is operable to provide instructions to the control system to enable or disable one or more of the plurality of devices.

In some embodiments, the server is in communication with a computer device at a service provider operable to provide information to the server regarding approved therapies for the first patient support apparatus.

In some embodiments, the server is operable to request approval for a therapy to be enabled on the first patient support apparatus from the service provider through the computer device.

In some embodiments, the first patient support apparatus includes a user input device coupled to the control system, the user input device operational to receive a user input requesting enablement or disablement of a therapy device and communicate the request to the server.

In some embodiments, the server is operable to transmit an authorization of the instructions to the control system to enable or disable the device.

In some embodiments, the server is in communication with a hospital information system, the hospital information system operational to receive a user input requesting enablement or disablement of a therapy device and communicate the request to the server.

In some embodiments, the server is operable to transmit an authorization of the instructions to the control system to enable or disable the devices through the hospital information system to the control system.

According to another aspect of the present disclosure, a patient support apparatus comprises a controller including a processor in communication with a memory device, a plurality of features under control of the controller, and a plurality of user inputs in communication with the controller. The user inputs are operable to provide a signal to the controller indicative of a user input requesting enablement or disablement of at least one of the features. The memory device includes instructions that, when executed by the processor, cause the processor to detect a signal from one the user inputs indicative of a requested change in the operational state of at least one of the features. The memory device includes further instructions that, when executed by the processor, cause the processor to transmit the request for a change in the operational state of at least one of the features to an authorization entity. The memory device includes further instructions that, when executed by the processor, cause the processor to monitor for a signal from the authorization entity that the change in the operational state of at least one of the features is permitted. The memory device includes further instructions that, when executed by the processor, causes the processor to, if the change in the operational state of at least one of the features is permitted, log the request, and enable the feature.

In some embodiments, the memory device includes further instructions that, when executed by the processor, causes the processor to activate the feature.

In some embodiments, the memory device includes further instructions that, when executed by the processor, causes the processor to, if the requested change in the operational state of at least one of the features is not permitted, communicate the denial of the request.

In some embodiments, the memory device includes further instructions that, when executed by the processor, causes the processor to monitor for a signal from the authorization entity indicative that an alternative feature is permissible, and, if an alternative feature is permissible, communicate the permissible alternative feature to the requester.

In some embodiments, the memory device includes further instructions that, when executed by the processor, causes the processor to determine if the permissible alternative feature is an acceptable substitute, and, if the alternative feature is an acceptable substitute, log the feature request.

In some embodiments, the memory device includes further instructions that, when executed by the processor, causes the processor to activate the alternative feature.

In some embodiments, the memory device includes further instructions that, when executed by the processor, causes the processor to monitor for deactivation of the feature. The memory device includes further instructions that, when executed by the processor, causes the processor to, if the feature is deactivated, transmit a signal that the deactivation has occurred to the authorization entity. The memory device includes further instructions that, when executed by the processor, causes the processor to monitor for a signal from the authorization entity authorizing deactivation of the feature. The memory device includes further instructions that, when executed by the processor, causes the processor to, if the signal from the authorization entity authorizing deactivation of the feature is received, deactivate the feature.

In some embodiments, the memory device includes further instructions that, when executed by the processor, causes the processor to transmit information regarding the usage of a feature to a third party to be used to establish a bill for use of the feature.

According to yet another aspect of the present disclosure, a patient support apparatus comprises a controller including a processor in communication with a memory device, a plurality of features under control of the controller, and a plurality of user inputs in communication with the controller. The user inputs are operable to provide a signal to the controller indicative of a user input requesting enablement or disablement of at least one of the features. The memory device includes instructions that, when executed by the processor, cause the processor to detect the occurrence of an event. The memory device includes further instructions that, when executed by the processor, causes the processor to determine whether to log the event. The memory device includes further instructions that, when executed by the processor, causes the processor to determine the nature of the event. The memory device includes further instructions that, when executed by the processor, causes the processor to respond to the event by communicating the event occurrence to a computer system resident at a third party.

In some embodiments, the memory device includes further instructions that, when executed by the processor, causes the processor to determine the nature of the event by distinguishing the event as either a patient event, a maintenance event, or a feature request event.

In some embodiments, the memory device includes further instructions that, when executed by the processor, causes the processor to respond to a patient event by communicating the patient event to a remote caregiver, wait for a signal from the remote caregiver in response to the event, and act on the response from the remote caregiver to change an operating parameter of the patient support apparatus.

In some embodiments, the memory device includes further instructions that, when executed by the processor, causes the processor to respond to a maintenance event by communicating the maintenance to a remote entity, wait for a signal from the remote entity in response to the event, and act on the response from the remote entity to change an operating parameter of the patient support apparatus.

In some embodiments, the memory device includes further instructions that, when executed by the processor, causes the processor to respond to the feature request event by, transmit the feature request to an authorization entity, monitor for a signal from the authorization entity that the feature request permitted, if the change in the operational state of at least one of the features is permitted, log the request, and enable the feature.

In some embodiments, the memory device includes further instructions that, when executed by the processor, causes the processor to transmit information regarding the usage of a feature to a third party to be used to establish a bill for use of the feature.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTIONS OF THE DRAWINGS

The detailed description particularly refers to the accompanying figures in which.

Figure 11:
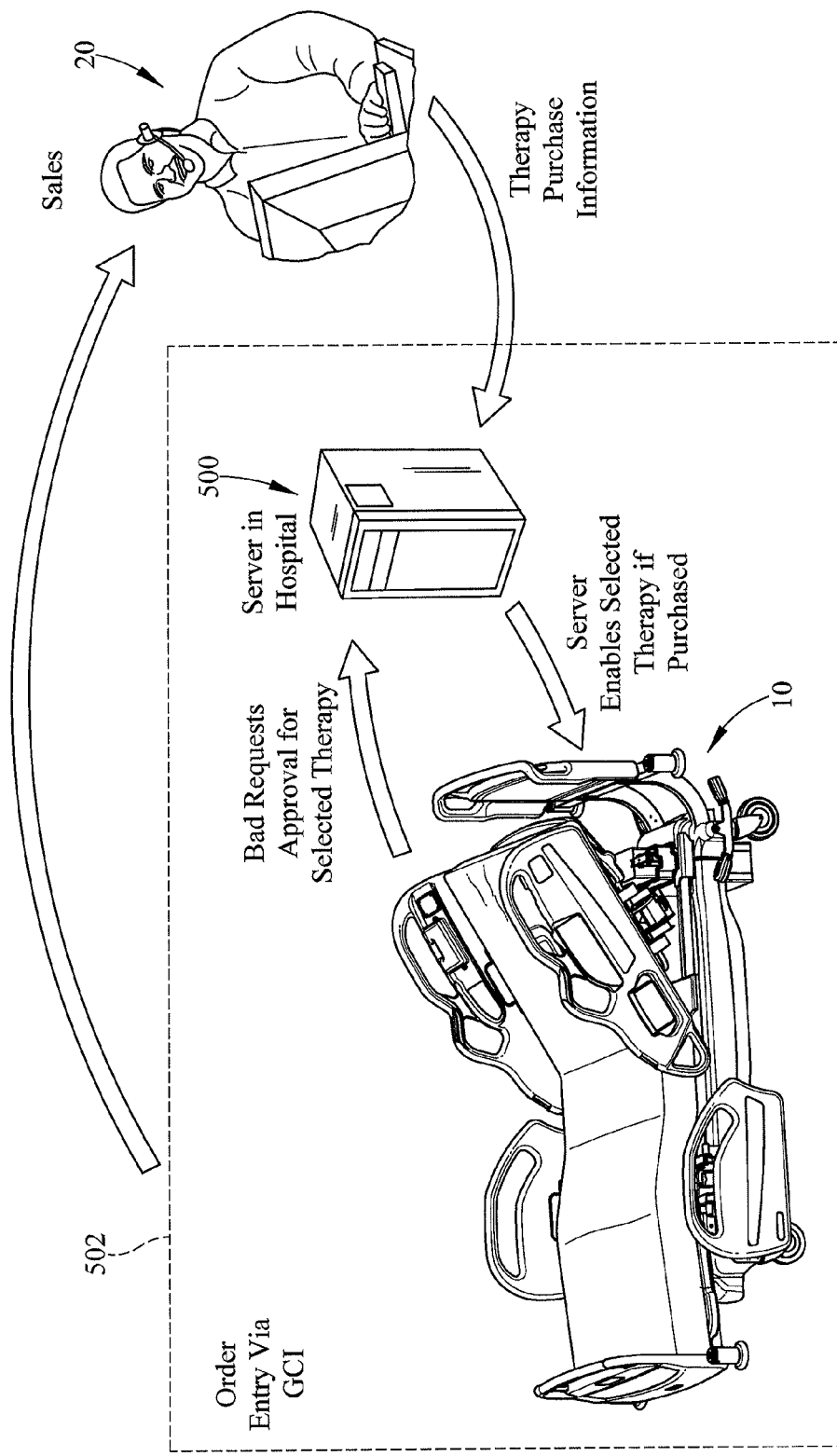
Figure 12:
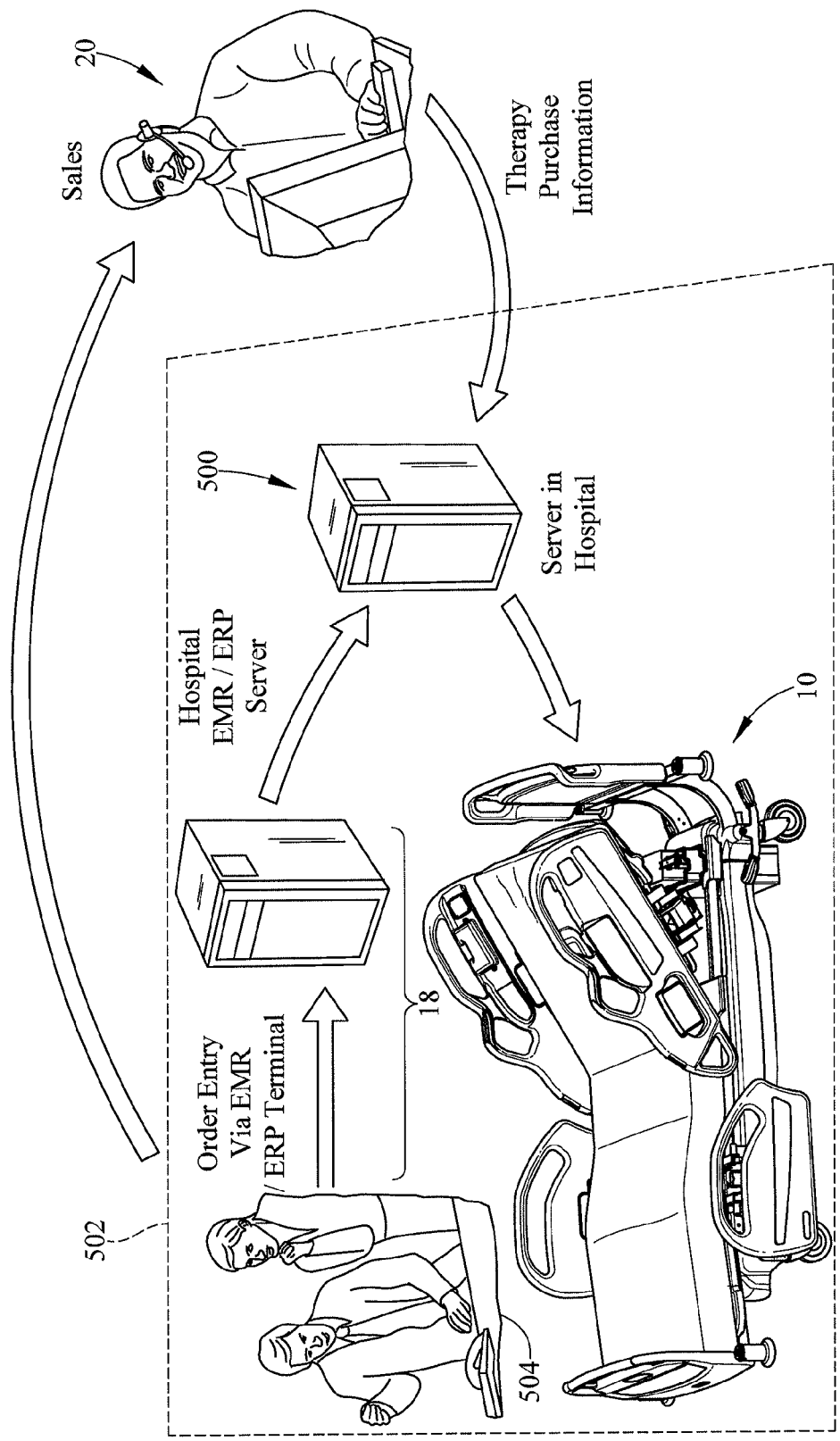

FIG. 11 is a diagrammatic representation of a second embodiment of a system that controls selectively enabled therapies on a patient support apparatus through an approval system that includes a service provider responding to a request from a caregiver input on the patient support apparatus; and FIG. 12 is a diagrammatic representation of a third embodiment of a system that controls selectively enabled therapies on a patient support apparatus through an approval system that includes a service provider responding to a request from a caregiver input on a terminal of a hospital information system.

DETAILED DESCRIPTION

Figure 1:
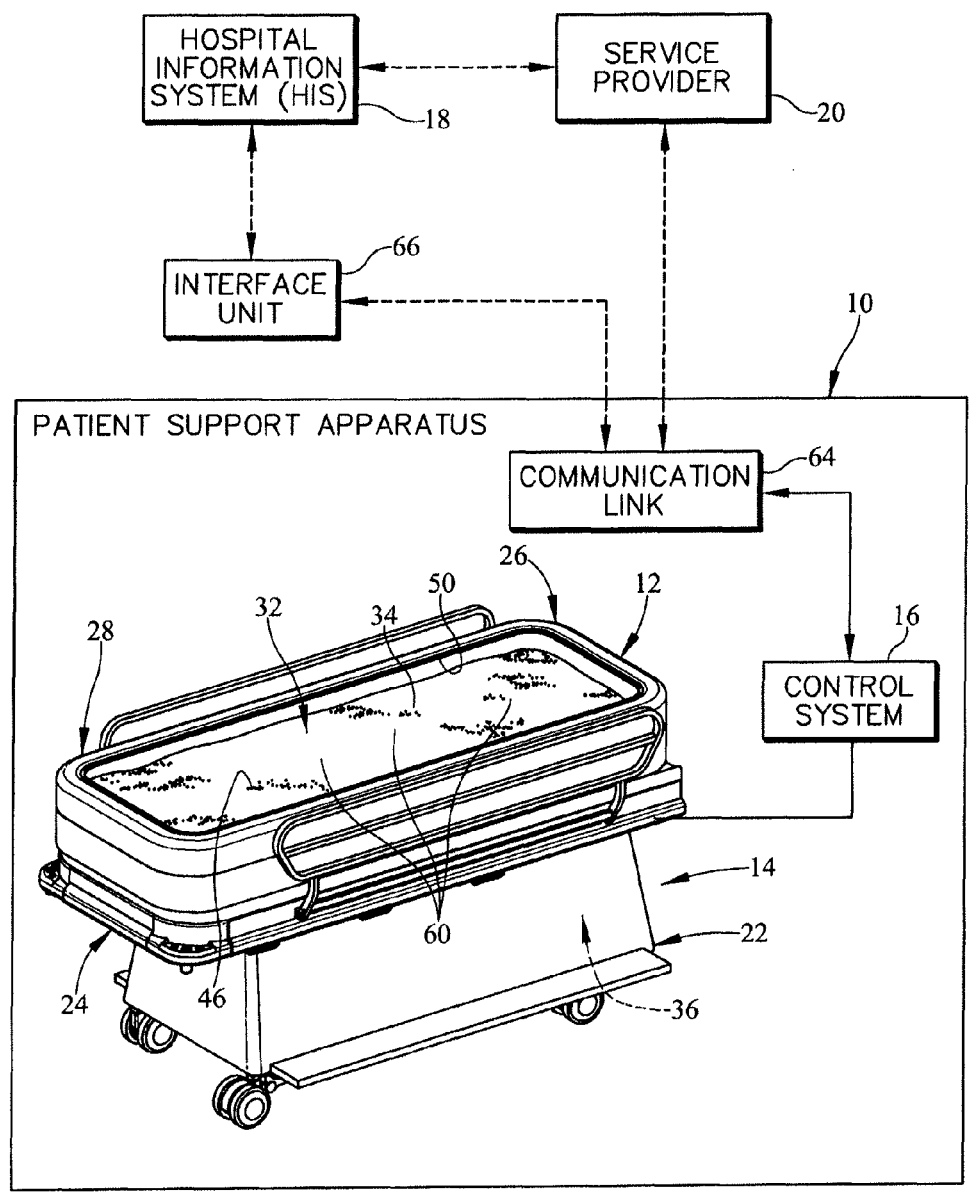
FIG. 1 is a diagrammatic and perspective view of a fluidized patient support apparatus including a control system and a communication link that may communicate with a hospital information system and a service provider.
Figure 2:
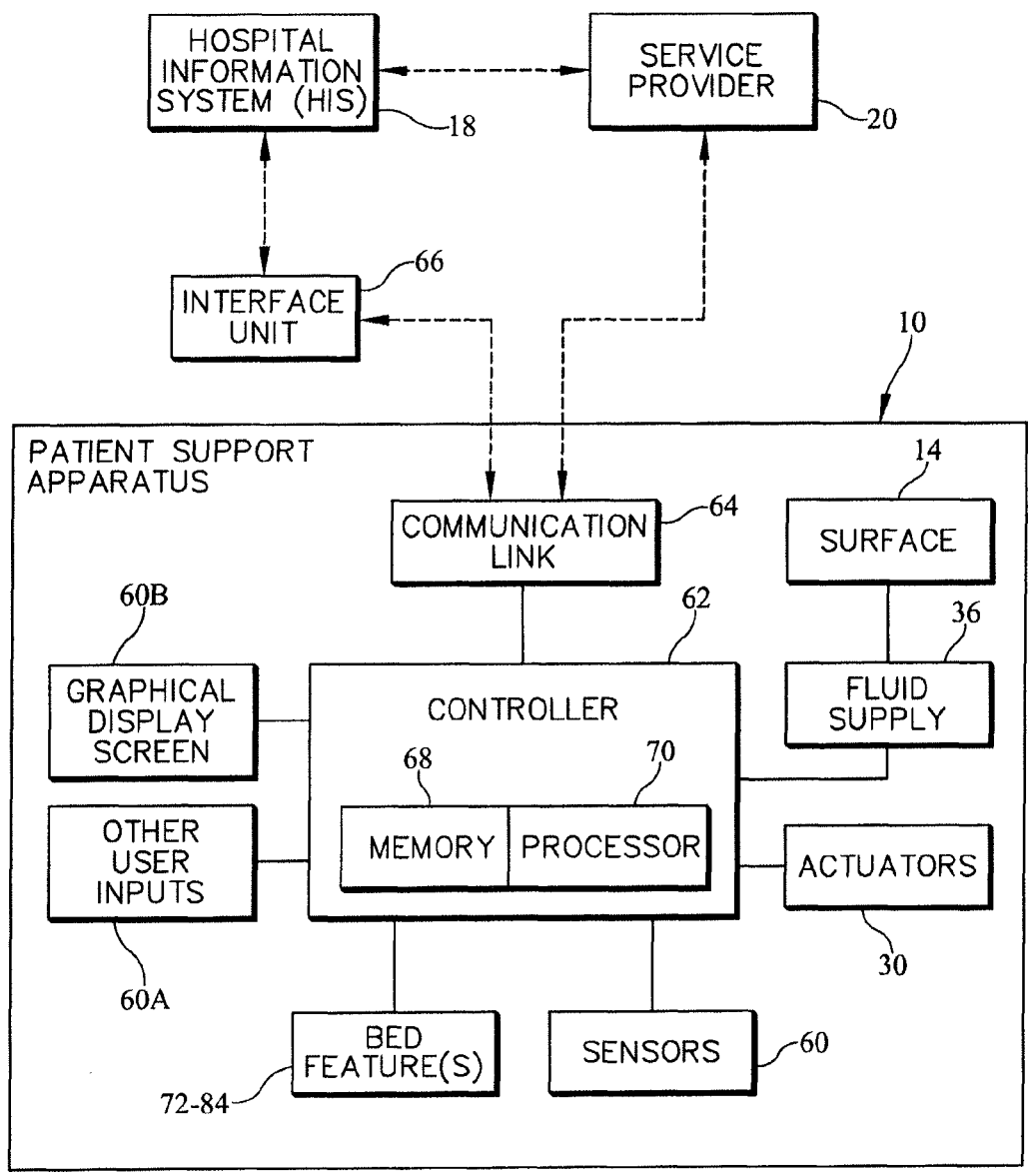
FIG. 2 is a diagrammatic view of a patient support apparatus showing the control system interacting with various components and features of the patient support apparatus.
Figure 3:
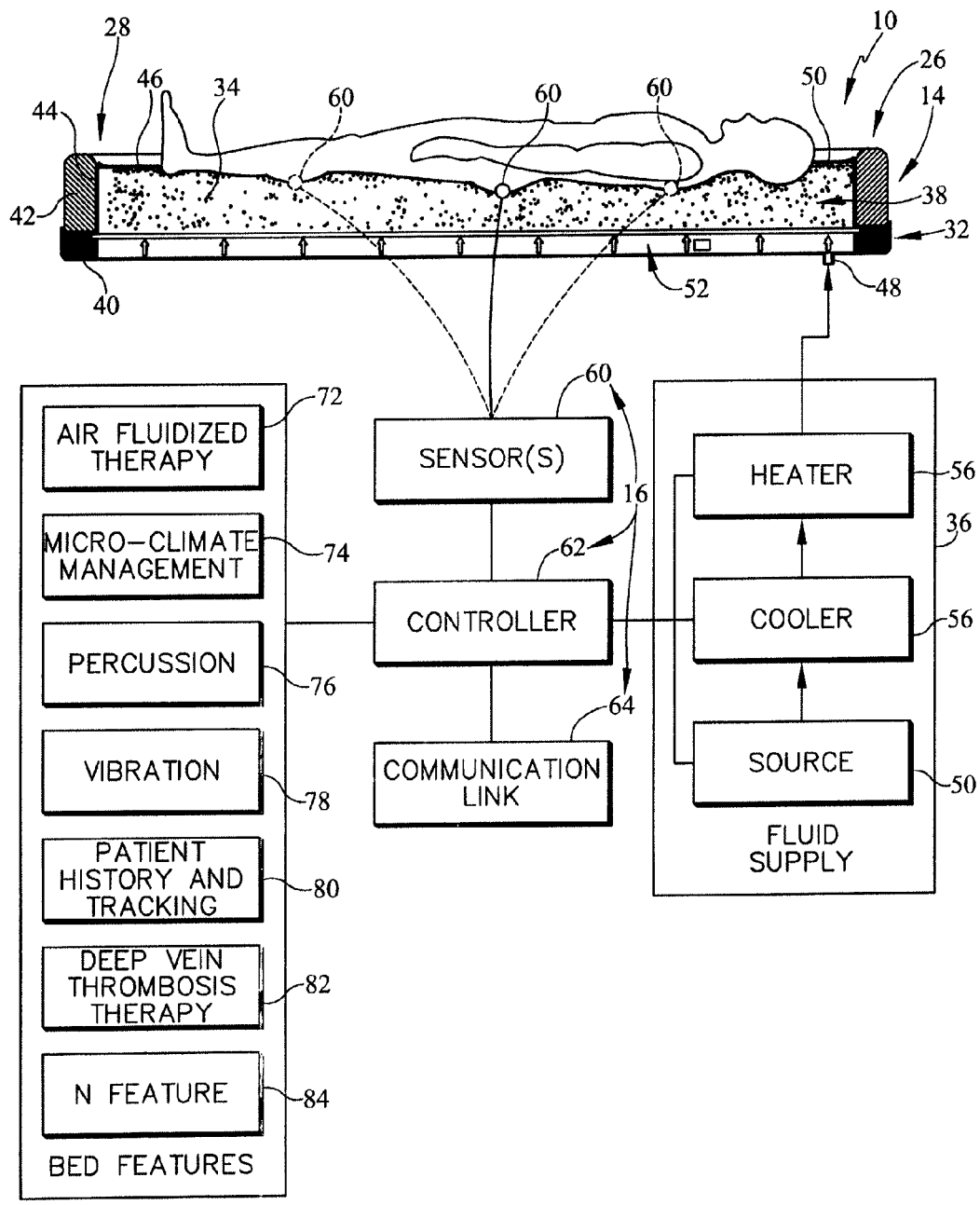
FIG. 3 is a diagrammatic and perspective view of the fluidized patient support apparatus of FIG. 1 showing that the control system may control various bed features and a fluid supply.

A patient support apparatus 10 in accordance with the present disclosure includes a patient support structure 12, a patient support surface 14, and a control system 16 as shown in FIGS. 1-3. The control system 16 is coupled to the patient support structure 12 and patient support surface 14 to control various bed features included in the patient support apparatus 10. In one example, the patient support surface 14 is a fluidization system 14 that is configured to provide an air fluidized therapy to a patient resting on the fluidization system 14 to minimize pressure ulcer formation on the patient. The air fluidized therapy is a bed feature that is activated, managed, and controlled by the control system 16 as suggested in FIGS. 2 and 3.

As a further example, the control system 16 may be configured to communicate with a hospital information system 18 and a service provider 20 to obtain permission to take various actions, request and receive instructions from caregivers and the service provider 20. The control system 16 may also communicate when various bed features are in use so that billing efficiency may be maximized. As an example, the control system 16 may determine that the air fluidized therapy was only in use for a brief period time, and thus, the caregiver and patient are only charged the brief period of time the bed feature was in use.

As shown in FIG. 1, the patient support structure 12 includes a lower frame 22 and an upper frame 24. The lower frame 22 is adapted to rest on and be supported by ground underlying the lower frame 22. The upper frame 24 is coupled to the lower frame 22 to move relative to the lower frame 22. In one example, the upper frame 24 may move vertically up and down, may tilt so that a head end 26 is higher than a foot end 28, or the foot end 28 is higher than the head end 26. The control system 16 is coupled to actuators 30 included in the patient support structure 12 to control to control movement of the patient support structure 12 as suggested in FIG. 2.

The patient support surface 14 includes, for example, a tank system 32, a fluidizable medium 34, and a fluid supply 36 as shown in FIG. 3. The tank system 32 is coupled to the upper frame 24 to move therewith and is formed to include a space 38 therein. The fluidizable medium 34 is located in the space 38 and contained by the tank system 32. The fluid supply is coupled to the tank system 32 to cause fluid under pressure to be moved through the fluidizable medium 34 so that the fluidizable medium is fluidized.

The tank system 32 includes a tank base 40, a tank liner 42, a tank bladder 44, and a filter cover 46 as shown in FIG. 3. In one illustrative embodiment, the tank base 40 and the tank liner 42 are made of a low or substantially no air-loss material, such as, for example, a polyurethane-backed nylon fabric material, and the tank bladder 44 is composed of a substantially no air loss polymeric material and filled with a fluid, such as, air. The tank base 40 is coupled to the upper frame 24 by tank fasteners (not shown) and includes an inlet 48 that couples to the fluid supply 36. The tank liner 42 and the tank bladder 44 are coupled together to form the sides of the tank system 32. The tank base 40 is coupled with the tank liner 42 and the tank bladder 44 to define an opening 50 arranged to open into the space 38 as shown in FIG. 3.

The filter cover 46 is positioned over the opening 50 and is coupled to the tank liner 42 as shown in FIG. 3. The filter cover 46 is coupled to the tank liner 42 by fasteners which may be zippers, buttons, snaps, turn-buttons, hook and loop fasteners, or any other suitable alternative. The tank base 40, the tank liner 42, the tank bladder 44, and the filter cover 46 cooperate to define the space 38 therebetween that contains the fluidizable medium 34 and a diffuser 52. The filter cover 46 is configured to allow fluid, such as, bodily fluids and air, to pass there through while preventing the fluidizable medium 34 from passing through. The filter cover 46 is also configured to provide sufficient support to minimize or eliminating hammocking from occurring when a person is supported by the fluidized fluidizable medium 34 so that the person is properly supported.

The diffuser 52 is configured to support the fluidizable medium 34 thereon and provide substantially uniform fluid flow to the fluidizable medium 34 from the fluid supply 36 as suggested, for example, in FIG. 3. Fluid supplied by the fluid supply passes through the diffuser 52 and into the fluidizable medium 34 to cause the fluidizable medium 34 to become fluidized.

The fluid supply 36 is configured to supply fluid having various fluid properties to the diffuser. The fluid properties include pressure, relative humidity, and temperature. As shown, for example in FIG. 3, the fluid supply 36 includes a source 54, a cooler 56, and a heater 58. The source 54 is configured to provide the fluid at a pressure requested by the control system 16. The cooler 56 is configured to cooperate with the source 54 to withdraw heat from the fluid so that the temperature of the fluid is reduced and relative humidity is controlled. The heater is configured to cooperate with the source 54 and the cooler 56 to control the output temperature of the fluid so that patient comfort and health is maximized.

The control system 16 is also coupled to each component of the fluid supply 36 to control the fluid properties of the fluid as it passes through the fluidizable medium 34. The control system 16 may command the source 54 to provide the fluid at various pressures and flow rates. The control system 16 may command the cooler 56 to withdraw heat from the pressurized fluid so as to remove excess humidity and achieve a desired relative humidity of the pressurized fluid and provide cool pressurized fluid to the patient when desired. The control system 16 may also command the heater 58 to add heat to the pressurized fluid after the cooler 56 has controlled for humidity so that the output temperature is configured to maximize patient comfort and health.

The control system 16 may vary the pressure, humidity, and temperature of fluid to accomplish various bed features. In one example, the control system 16 and the fluid supply 36 cooperate to provide air fluidized therapy. Additional features of air fluidized therapy are discussed in U.S. application Ser. No. 13/246,886, filed Sep. 28, 2011 and entitled "SYSTEMS, METHODS, AND DEVICES FOR FLUIDIZING A FLUIDIZABLE MEDIUM," which is hereby incorporated in its entirety by reference herein. In another example, the control system 16 and the fluid supply 36 cooperate to provide micro-climate management of the patient support surface 14. Additional features of micro-climate management are discussed in U.S. Application No. PCT/US09/40661, filed Apr. 15, 2009 and entitled "MICROCLIMATE MANAGEMENT SYSTEM," which is hereby incorporated in its entirety by reference herein. In still yet another example, the control system 16 and the fluid supply 36 cooperate to provide adverse condition detection, assessment, and response in the patient support surface 14. Addition discussion of systems for adverse condition detection, assessment, and response is found in U.S. Application No. 61/650,436, filed May 22, 2012 and entitled "ADVERSE CONDITION DETECTION, ASSESSMENT, AND RESPONSE SYSTEMS, METHODS AND DEVICES," which is hereby incorporated in its entirety by reference herein.

As shown in FIGS. 1 and 3, the control system 16 further includes one or more sensors 60. The sensor 60 is configured to provide a sensor signal representative of one or more sensed parameters, such as, for example, temperature, relative humidity, skin color, or air flow. In some embodiments, the sensors 60 may detect chemical characteristics such as chemicals that indicative of incontinence or of skin breakdown. In one example, the sensor 60 is configured sense pressure applied by the patient resting on the patient support surface 14. The pressure sensor 60 may be coupled to the filter cover 46 to sense pressure exerted on the patient by the filter sheet and underlying fluidizable medium 34.

The pressure sensor 60 may be used to develop a high interface pressure hot spot map that tracks the development of hot spots over time and determines when a predetermined threshold is exceeded. When the predetermined threshold is exceeded, the control system 16 recognizes this as a patient event which causes the control system 16 to take action as suggested in FIG. 4 and in more detail in FIGS. 6 and 7. In one example, the control system 16 may contact a caregiver notifying them of the patient event has occurred. U.S. application Ser. No. 13/609,776, filed Sep. 11, 2012 and entitled "PRESSURE ULCER DETECTION SYSTEMS AND METHODS" is hereby incorporated in its entirety by reference herein for disclosure related pressure sensors and methods of using pressure sensors to detect pressure ulcer formation.

In another example, the pressure sensor 60 may be used to develop a quantified Braden Assessment for pressure ulcer risk. Measures provided by pressure sensor 60 may be used to calculate objective values for sub-scores within the overall Braden score. The Braden score uses sub scores for mobility and activity which may be provided by pressure sensor 60. The Braden score also uses share and moisture sub scores which may be provided by other sensors. The control system 16 may be configured to monitor the Braden Assessment and determines a patient event occurs when the Braden Assessment estimate passes a predetermined threshold and take action as suggested in FIG. 4 and in more detail in FIGS. 6 and 7. In one example, the control system 16 may contact a caregiver notifying them of the patient event has occurred.

In yet another example, the pressure sensor 60 may be used to provide turn tracking of the patient. As an example, the control system 16 may use the sensor date provided by pressure sensor 60 to determine when a patient has turned on the patient support surface 14. If the patient has not moved relative to the patient support surface 14, the control system 16 for a predetermined time period, the control system 16 may again determine a patient event has occurred and take action as suggested in FIG. 4 and in more detail in FIGS. 6 and 7. In one example, the control system 16 may contact a caregiver notifying them that the patient event has occurred.

In another example, the sensor 60 is configured sense temperature. The temperature sensor 60 may be woven into the filter cover 46 or applied to the surface of the filter cover 46. In one example, the temperature sensor 60 is configured to provide a signal representative of the temperature measured. In another example, the temperature sensor 60 is configured to provide a signal only if a predetermined threshold temperature is sensed. Such temperature readings may be useful for providing feedback to the control system 16 to change the temperature of fluid exiting the fluid supply 36 so that patient comfort and health may be maximized.

In still yet another example, the sensor 60 may be a humidity sensor. The humidity sensor 60 may be integrated with the filter cover 46 or arranged to lie in close proximity to the filter cover 46 in the fluidizable medium 34. The humidity sensor 60 may be used to measure the relative humidity of the fluid supplied by the fluid supply 36 to provide feedback to the control system 16. In another example, the humidity sensor 60 may be used to measure the humidity of the fluid after passing over the patient to detect if patient sweating is occurring or likely to occur.

In yet another example, the sensor 60 may be a moisture sensor. The moisture sensor 60 may be configured to provide a signal that is indicative that a predetermined amount of moisture is detected between the patient and the patient support surface. The moisture sensor 60 may also be used to detect the occurrence of an incontinence by the patient. Incontinence may be detected and determined to be a patient event by the control system 16. As a result, the control system 16 may take one or more predetermined actions such as contacting the caregiver.

In another example, the sensor 60 may be configured to sense one or more pathogens. The detection of a pathogen may considered a patient event that requires associated action to be taken either through caregiver intervention or as a predetermined action to be taken automatically by the patient support apparatus 10 in response to command by the control system 16. U.S. application Ser. No. 13/654,649, filed May 16, 2012 and entitled "PATHOGEN DETECTION SYSTEMS AND METHODS" is hereby incorporated in its entirety by reference herein for disclosure related detection of pathogens and responses to the detection of pathogens.

In still yet another example, the sensor 60 may be embodied as a user input, for example, integrated in the operation of graphical display screen 60B including a touch screen or virtual keyboard as shown in FIG. 2. However, the sensor 60 may be other user inputs 60A such as a physical keyboard, a mouse, a microphone, or a video camera that is configured to receive user input. In one example, the touch screen 60 is coupled to the patient support apparatus 10. A caregiver or patient may engage the touch screen 60 which captures the input and communicates the input to the control system 16. The control system 16 may analyze the user input and take appropriate action. Such action may be to communicate the user input to the hospital information system. Such action may be to send a communication to a doctor or service provider requesting verification of the user input. The action may also be to implement the user input such as changing the height of the patient support surface 14 relative to the ground.

The control system 16 includes, for example, the sensor 60, a controller 62, and a communication link 64 as shown in FIG. 2. The sensor 60 is coupled to the controller 62 to provide a sensor signal to the controller 62. The communication link 64 is coupled to the controller 62 and configured to send data from the controller 62 to an interface unit 66 that may communicate with the hospital information system 18 or the service provider 20. The communication link 64 may also be configured to communicate directly with the hospital information system 18 and the service provider 20 without the interface unit 66. The communication link 64 is also configured to receive data and transmit it to the controller 62 for processing.

The controller 62 includes memory 68 and a processor 70 as shown in FIG. 3. The memory 68 is coupled to the processor 70 and configured to store instructions to be performed by the processor 70 and data received from the processor or calculated by the processor. The instructions are configured to provide, in one example, a process 200 of operating the patient support apparatus 10 as shown in FIGS. 4-9. The processor 70 is coupled to the sensor 60 and configured to receive the sensor signal provided by the sensor. The processor 70 then calls on instructions stored in memory 68 and executes the process 200.

The process 200 includes a series of decision steps, process steps, and subroutines as shown in FIGS. 4-9. The process 200 begins with a process step 202 which powers on the patient support apparatus 10. The process 200 then proceeds to another process step 204 in which an event is detected by the sensor 60 and the sensor 60 sends the sensor signal to the processor 70. The process 200 then proceeds to a decision step 206 in which the processor 70 determines whether the event should be logged with the hospital information system 18, the service provider 20, or stored in the memory 68 of the control system 16. If the event should be logged, the process 200 proceeds to a logging subroutine 208 which logs the event. If the event should not be logged, the process 200 proceeds to subsequent decisions steps where the type of event is determined and appropriate actions are taken based on the event type.

Figure 4:
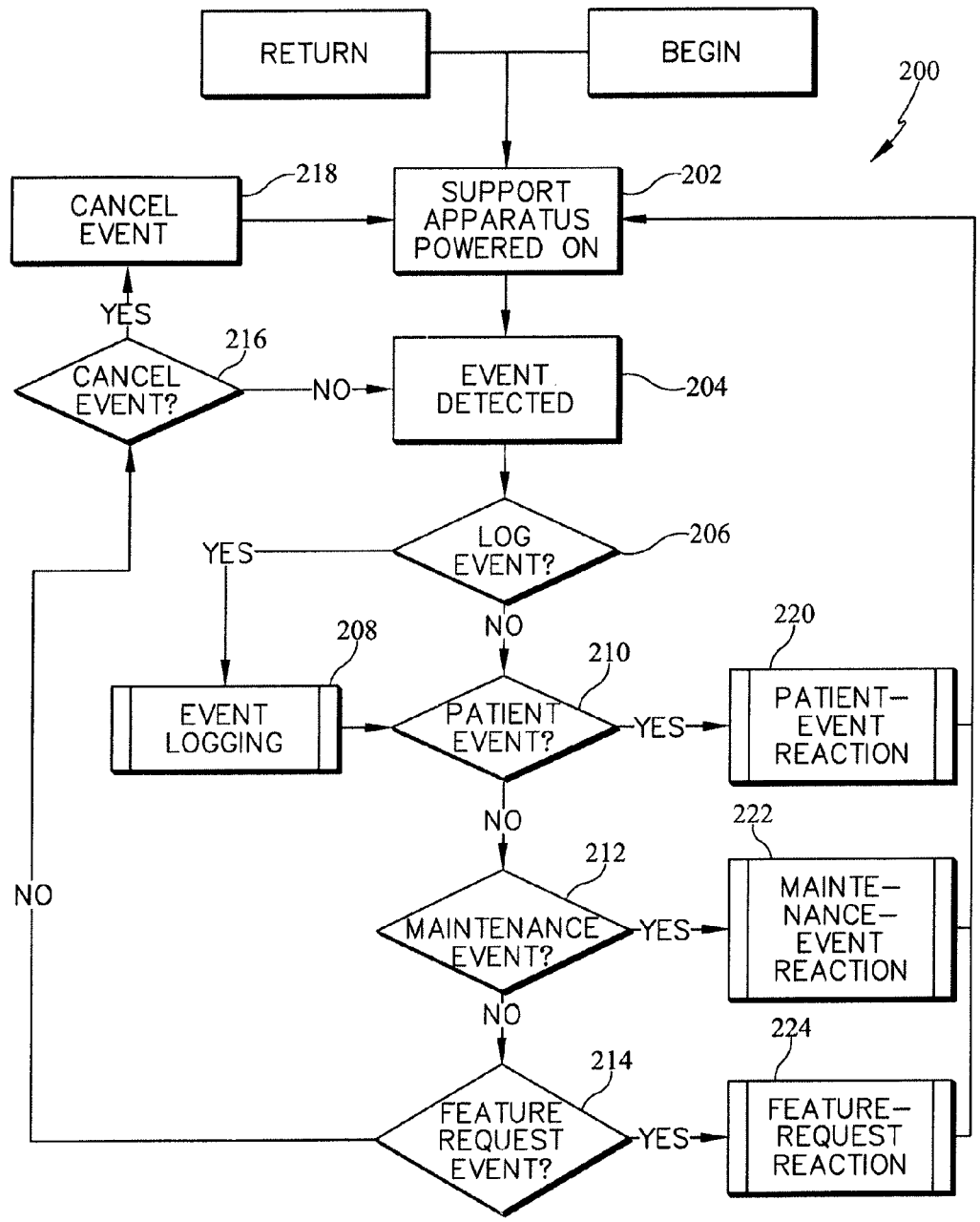
FIG. 4 is a flowchart of a control routine for the control system.

After the decision step 206 and the logging subroutine 208, the process 200 proceeds to a decision step 210 which determines if the event is a patient event as shown in FIG. 4. If decision step 210 determines that the event is a patient event, the process 200 proceeds to a patient-event subroutine 220 which is an appropriate reaction to the patient event as shown in FIG. 4. If the event is not a patient event, the process proceeds to a decision step 212 which determines if the event is a maintenance event. If the decision step 212 determines that the event is a maintenance event, the process 200 proceeds to a maintenance-event subroutine 222 which is a reaction to the maintenance event as shown in FIG. 4. If the event is not a maintenance event, the process 200 proceeds to a decision step 214 which determines if the event is a feature-request event. If decision step 214 determines that the event is a feature-request event, the process 200 proceeds to a feature-request subroutine 224 which is a reaction to the feature request event as shown in FIG. 4.

When the event is determined not to be one of a patient event, a maintenance event, or a feature-request event, the process 200 proceeds to a decision step 216 which determines if the event should be canceled. If the event should be canceled, the process 200 proceeds to a process step 218 that cancels the event and process 200 proceeds back to the process step 202 which is the patient support apparatus 10 is powered on. If the event should not be canceled, the process 200 returns to the process step 204 in which the event is detected by sensor 60 to see if the event should go through the process 200.

Decision step 210 determines whether the event detected by sensor 60 is a patient event. A patient event is an event which is caused by a patient condition such as sweating on incontinence. Characteristics describing such events are stored in memory 68, on computers in the hospital information system 18, or computers at the service provider. The process 70 compares the obtained sensor data to the stored characteristics to determine whether an event should be classified as a patient event. In one illustrative example, incontinence may be defined as substantial moisture on the patient support surface detected by sensor 60. When sensor 60 detects substantial moisture, the sensor signal is communicated to processor 70 where the processor compares the sensor signal to stored values in memory 68 and determines whether or not the detected event is a patient event.

If the detected event is a patient event, the patient-event subroutine 220 is called by the process as shown in FIG. 4. The patient-event subroutine 220 begins at a decision step 226 which determines whether the patient support apparatus 10 requires permission from a caregiver to take an action. If the patient support apparatus 10 does not require permission from the caregiver, the patient-event subroutine 220 proceeds to a process step 228 in which a predetermined action occurs. In one illustrative example, sensor 60 detects that the patient has begun to sweat. The processor 70 then looks in memory 68 to determine if a predetermined action may be taken without caregiver permission. In the illustrative example, the processor 70 may determine that increasing air flow via fluid supply 36 may be done without caregiver permission and the processor 70 commands the fluid supply to increase a fluid flow rate to minimize sweating of the patient.

If the patient support apparatus 10 does require permission, the patient-event subroutine 220 proceeds a subsequent decision step 230 which determines whether permission may be given remotely from the patient support apparatus 10. If the permission may be given remotely, the patient-event subroutine 220 proceeds to a process step 232 which requests permission remotely from the caregiver. In one example, processor 70 uses communication link 64 to communicate with the caregiver via a computer in the hospital information system 18, a cell phone, tablet, or any other suitable alternative. The patient support apparatus 10 may communicate the type of patient event, the proposed predetermined action, the time of the event, the location, and any other information relevant to the decision of the caregiver. After notifying the caregiver, the patient-event subroutine 220 then proceeds a decision step 234. If permission may not be given remotely, the patient-event subroutine 220 then proceeds to a process step 236 which summons the caregiver to the patient support apparatus 10. Once the caregiver is at the patient support apparatus, the patient-event subroutine 220 proceeds to decision step 234.

Decision step 234 determines whether the caregiver is authorized to give permission. If the caregiver is authorized, the patient-event subroutine 220 proceeds to a decision step 238 which determines whether the caregiver gives permission. If the caregiver is not authorized, the patient-event subroutine 220 returns to the decision step 226 to determine whether permission is required for action and another caregiver can respond. If the caregiver is authorized, then the patient-event subroutine 220 proceeds to the decision step 238 which determines whether the caregiver has authorized the predetermined action of the patient support apparatus 10 as shown in FIG. 6A.

Figure 6A:
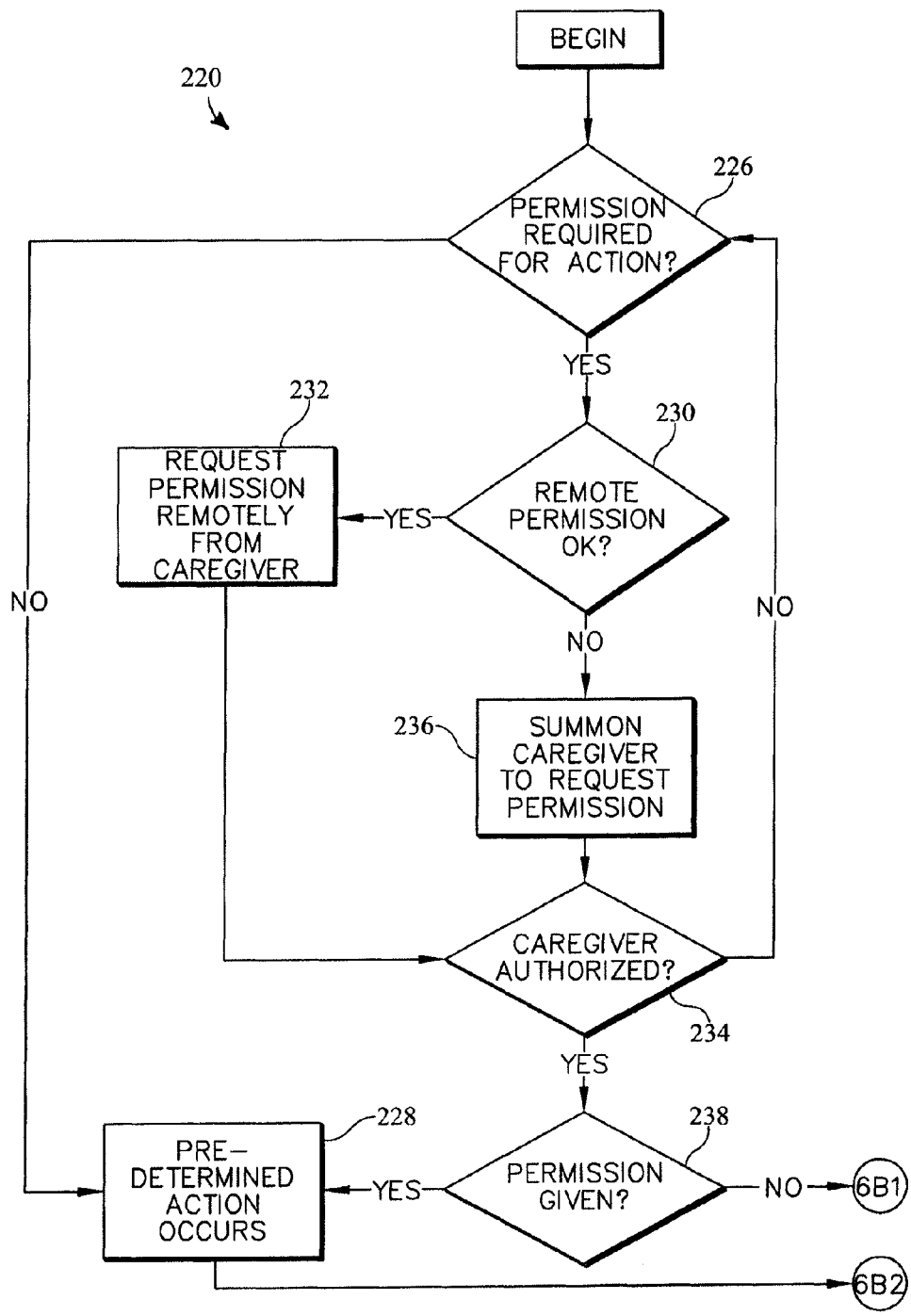
FIGS. 6A and 6B are a series of flow charts showing a sub-routine related to patient events included in the control routine of FIG. 4.
Figure 6B:
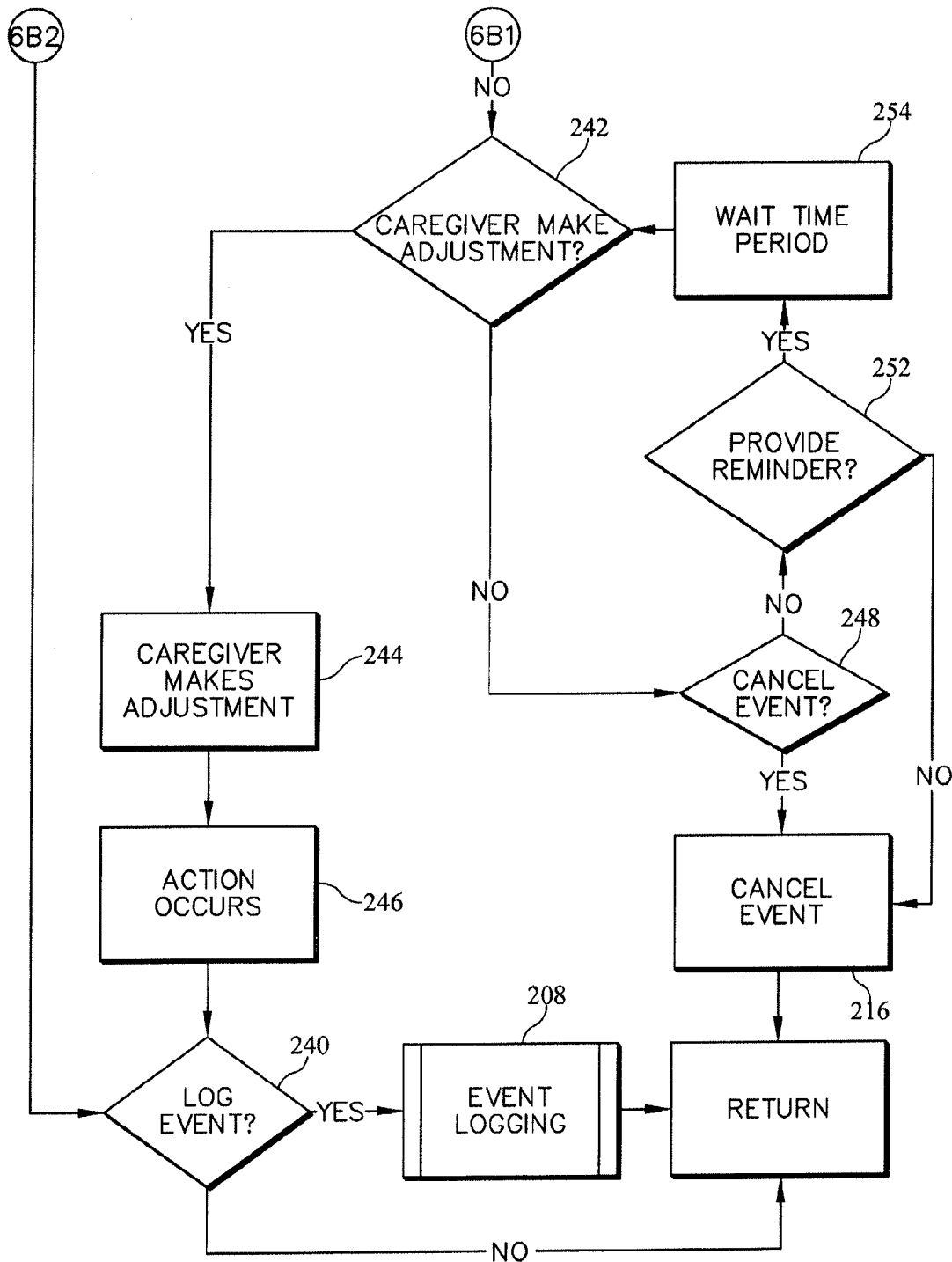

Decision step 238 determines whether the caregiver has authorized the predetermined action of the patient support apparatus 10 as shown in FIG. 6A. In one example, the caregiver may provide authorization by interacting with a user interface on the patient support apparatus, a computer in the hospital information system 18, or a mobile device. If the caregiver provides authorization, the patient-event subroutine 220 proceeds to the process step 228 which causes the patient support apparatus 10 to take the predetermined action. Once the predetermined action occurs, the patient-event subroutine 220 proceeds to a decision step 240 that determines if the predetermined action should be logged as shown in FIG. 6B. If the caregiver does not provide authorization for the predetermined action, the patient-event subroutine 220 proceeds to a decision step 242 which determines if the caregiver would like to make an adjustment to the predetermined action as show in FIG. 6B.

The decision step 242 of the patient-event subroutine 220 determines whether the caregiver desires to make an adjustment to the predetermined action of the patient support apparatus 10. If the caregiver desires to make an adjustment, the patient-event subroutine 220 proceeds to a process step 244 in which the caregiver makes the adjustment. The patient-event subroutine 220 then proceeds to a subsequent process step 246 in which the patient support apparatus 10 performs the adjusted action. In an example, the original predetermined action in response to an incontinence event may be to stop source 54 until a linen change has occurred. However, the caregiver, knowing that a patient may be at high risk of pressure ulcers, adjusts the predetermined action so that air flow is only reduced or blocked in certain areas on the patient support surface 14.

In the instance where the caregiver does not desire to make an adjustment, the patient-event subroutine 220 proceeds to a determination step 248 as shown in FIG. 6B. The determination step 248 determines whether the event should be canceled. The controller 62 may make this determination by asking the caregiver on a graphical user interface and capture an input provided by the caregiver. If the caregiver cancels the event, the patient-event subroutine 220 proceeds to a process step 218 which cancels the event. The patient-event subroutine 220 then returns back to process step 202 where the patient support apparatus is powered on. If the caregiver does not desire to cancel event, the patient-event subroutine 220 proceeds to a decision step 252 which determines if a reminder should be provided. If a reminder should be provided, the patient-event subroutine 220 proceeds to a process step 254 which waits a predetermined time period before advancing back to decision step 242 which determines whether the caregiver desires to make an adjustment. If no reminder is desired, then the patient-event subroutine 220 proceeds to the process step 218 as illustrated in FIG. 6B.

After the patient-event subroutine 220 has performed either the process step 246 or the process step 228, the patient-event subroutine 220 proceeds to the decision step 240 which determines whether performing the actions should be logged as shown in FIG. 6B. If the event should be logged, the patient-event subroutine 220 proceeds to the logging subroutine 208 where the action is logged in memory 68 of the control system 16 or communicate the log to the hospital information system 18. If the event should not be logged, the patient-event subroutine 220 proceeds to return to the process step 202 of the process 200 in which the patient support apparatus 10 is powered on.

When the control system 16 determines that the event detected at process step 204 is not a patient event, the process 200 proceeds to the decision step 212 as shown in FIG. 4. The decision step 212 determined whether the event detected is a maintenance event. In one illustrative example, the sensor 60 may be a differential pressure sensor 60 included in the fluid supply 36 that monitors the pressure drop across a filter include in the fluid supply 36. The differential pressure sensor may be configured to send a sensor signal to the control system 16 when the pressure drop reaches a certain amount indicating the filter should be changes. As a result, the control system 16 would compare this sensor signal with a comparative value and determine that this is a maintenance event.

Figure 7A:
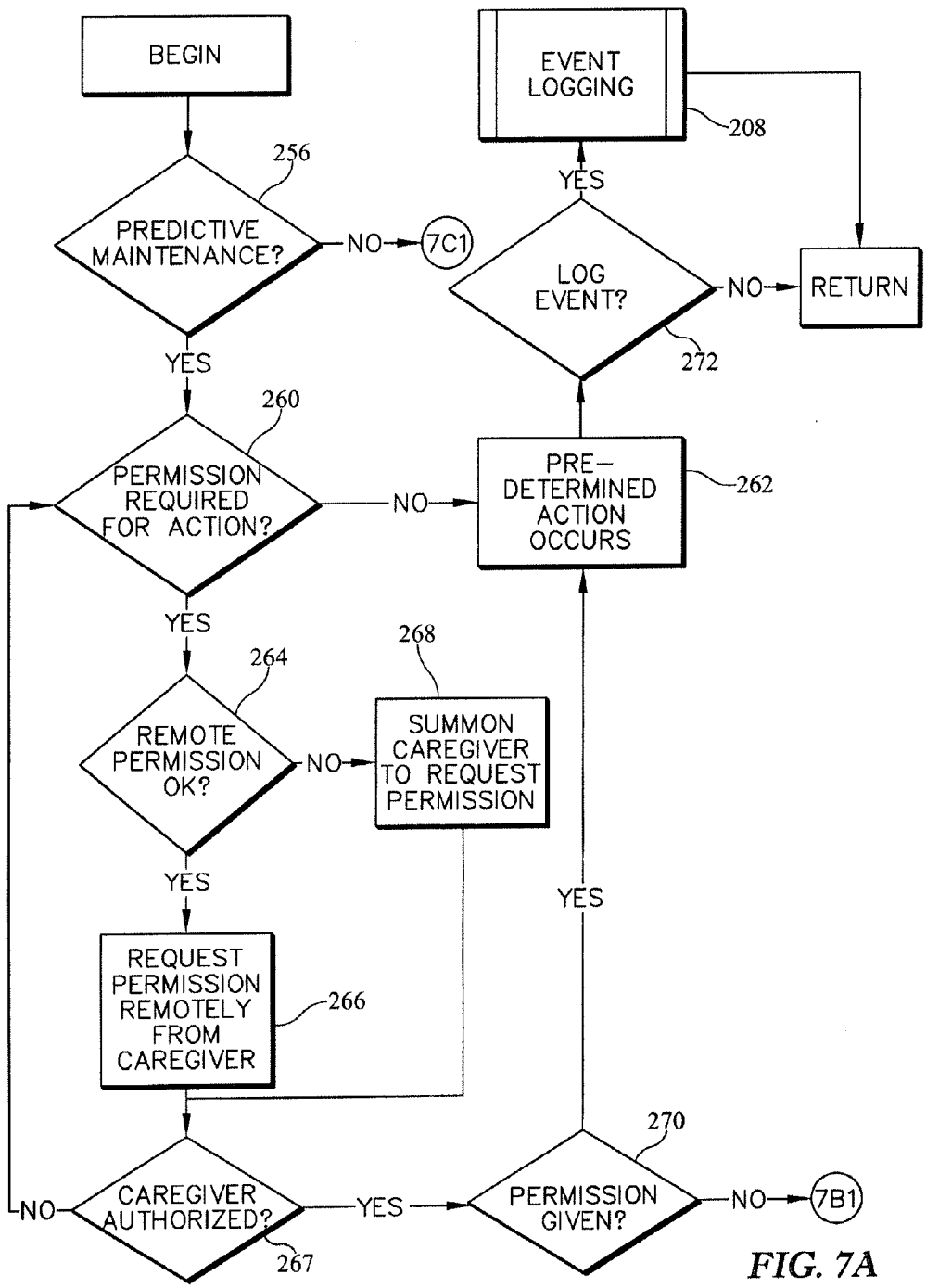
FIGS. 7A-7E are a series of flow charts showing a sub-routine related to maintenance events included in the control routine of FIG. 4.
Figure 7B:
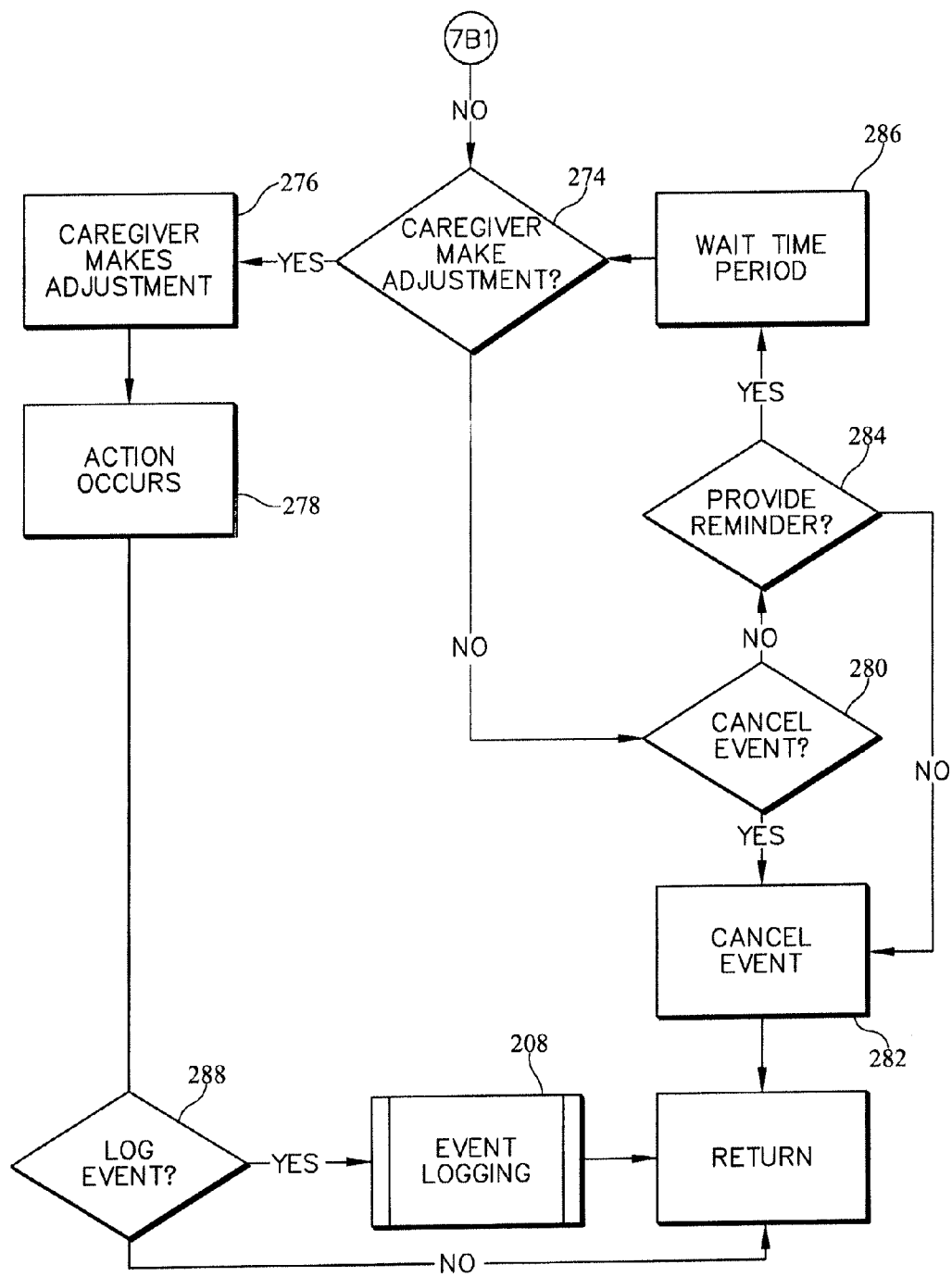
Figure 7C:
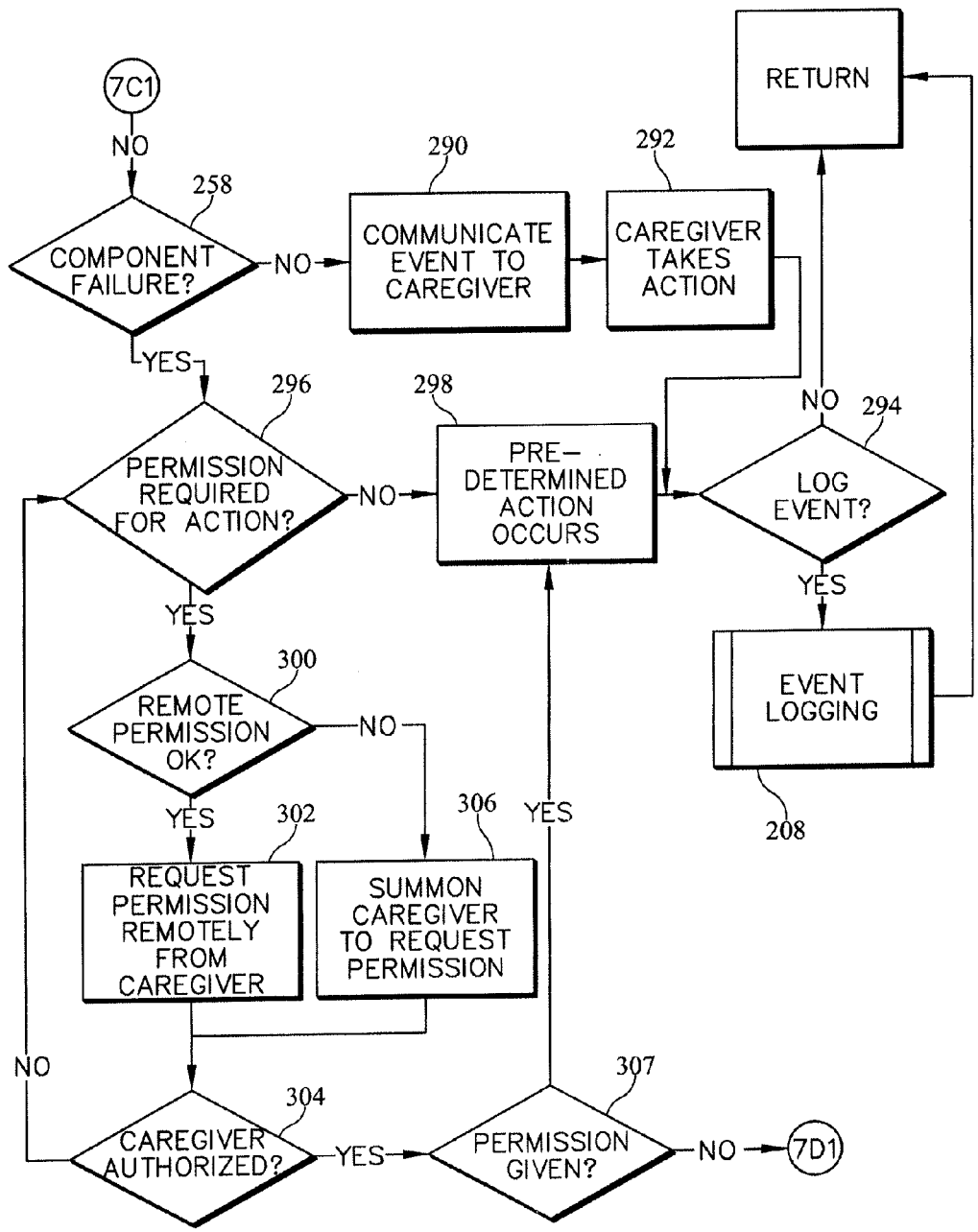
Figure 7D:
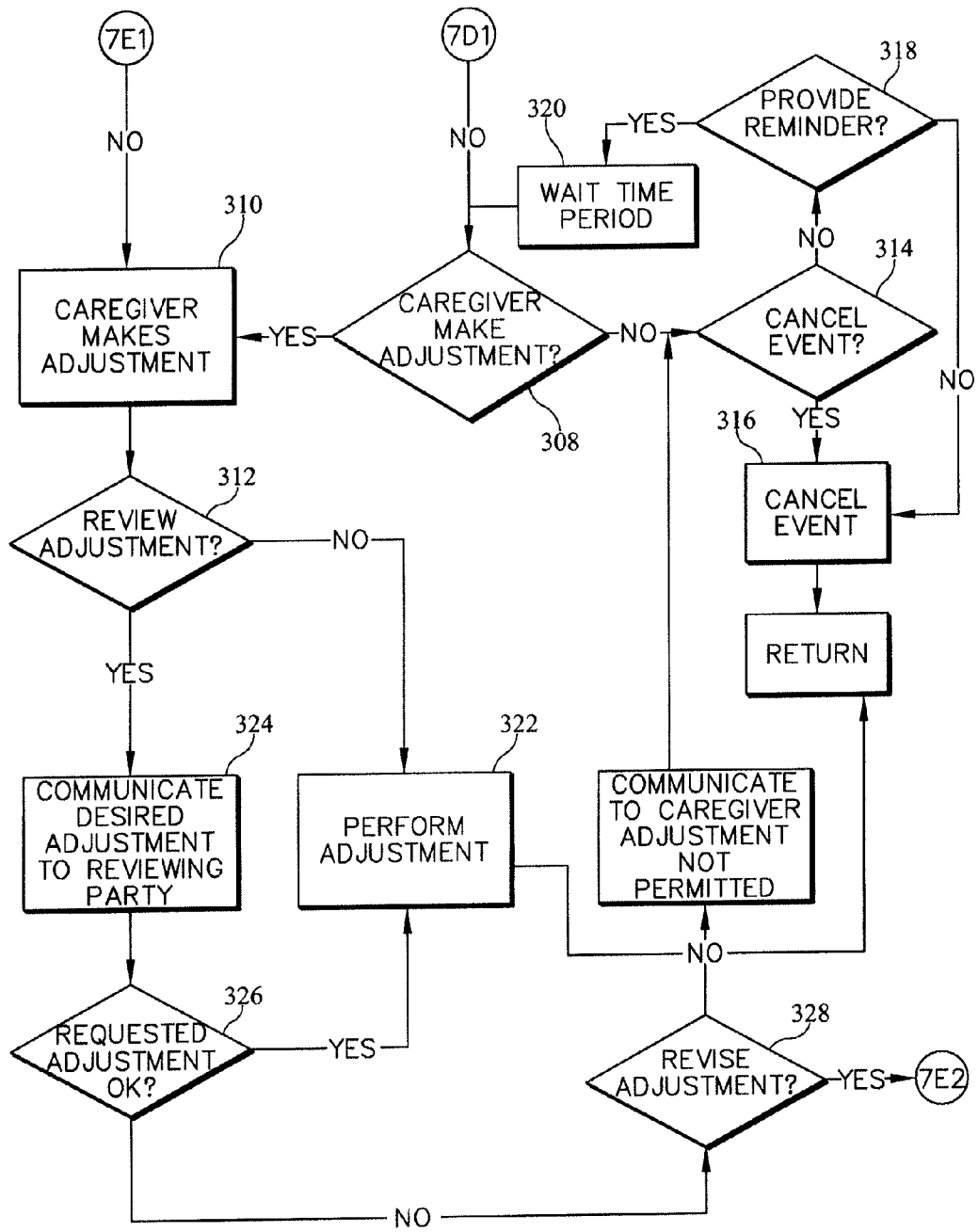
Figure 7E:
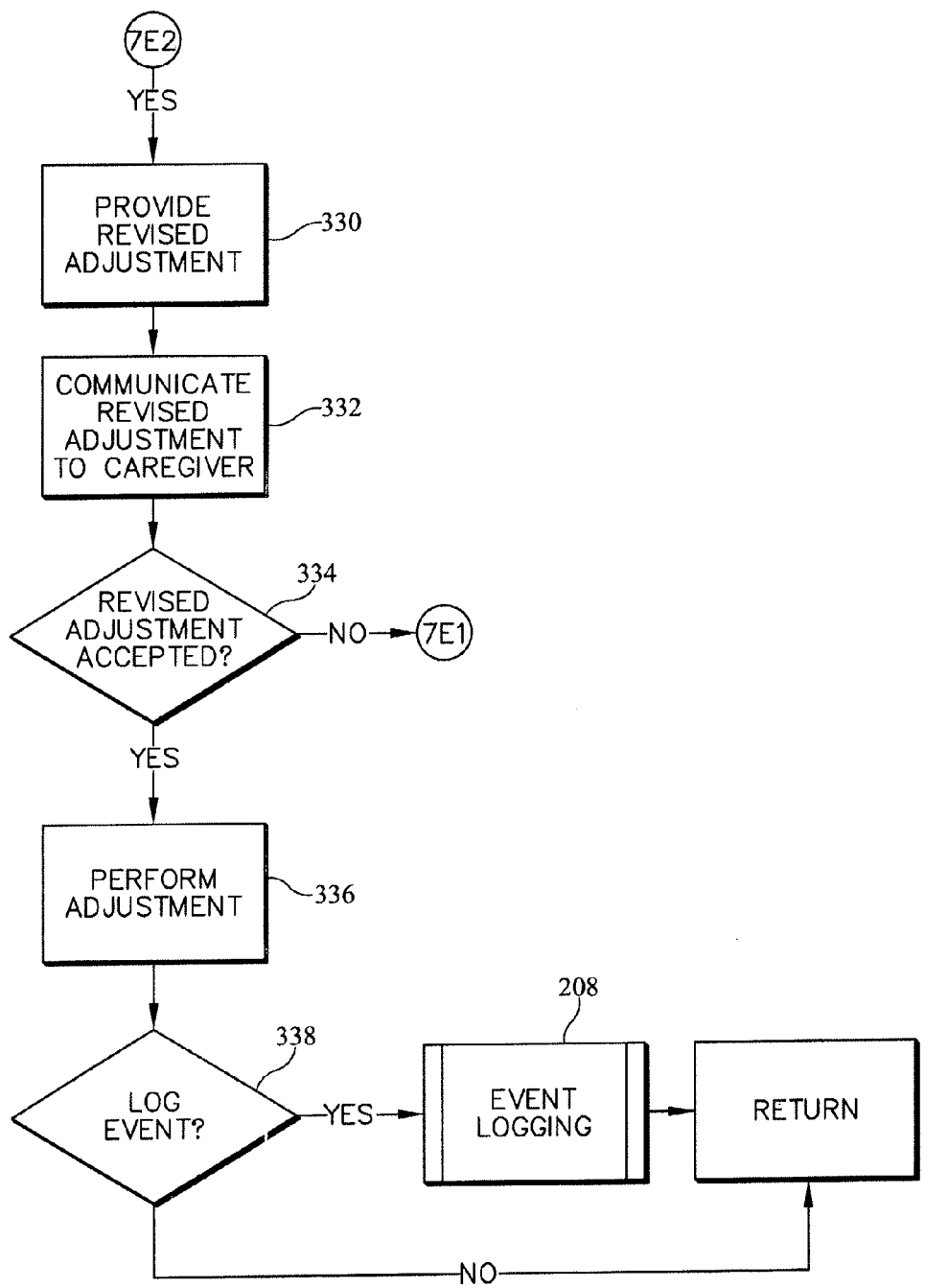

When the control system 16 determines that the event is a maintenance event in decision step 212, the process 200 then proceeds to the maintenance-event subroutine 222 as suggested in FIG. 4 and shown in detail in FIGS. 7A-7E. The maintenance-event subroutine 222 begins with a decision step 256 that determines if the event is related to predictive maintenance. Using the example from above where the pressure sensor 60 on the filter has been tripped, the control system 16 may determine that this is a predictive maintenance event that may be performed at a later time when the patient support apparatus 10 is not being used by a patient. If the control system 16 determines that the event is not a predictive maintenance event, the maintenance-event subroutine proceeds to a decision step 258 which determines whether the event is a component failure event. A component failure event may be that the same pressure sensor 60 now reads no pressure drop across the filter even though the control system 16 is calling for fluid to be provided by the source 54. Here, the control system 16 may determine that the source 54 has failed and that appropriate action should be taken as shown in FIGS. 7C-7E.

The maintenance-event subroutine 222 begins with the decision step 256 as shown in FIG. 7A. Decision step 256 determines if the event is a predictive maintenance event, like the need to change an air filter. When the control system 16 determines the event is a predictive maintenance event, the maintenance-event subroutine 222 proceeds to a decision step 260 which determines whether permission is required for the patient support apparatus 10 to take a predetermined action. If permission is not needed, the maintenance-event subroutine 222 proceeds to a process step 262 in which the patient support apparatus automatically takes a predetermined action. In one example, the predictive maintenance event could be the need to change an air filter. In this example, the control system 16 may automatically notify maintenance of the need to change the filter and schedule the bed not to be used after the current patient has been discharged.

If decision step 260 determines that permission is needed, the maintenance-event subroutine 222 proceeds to a subsequent decision step 264 which determines whether permission may be given remotely from the patient support apparatus. If permission may be given remotely, the maintenance-event subroutine 222 proceeds to a process step 266 which requests permission remotely from the caregiver. After notifying the caregiver, the maintenance-event subroutine 222 then proceeds a decision step 267. If permission may not be given remotely, the maintenance-event subroutine 222 then proceeds to a process step 268 which summons the caregiver to the patient support apparatus 10. Once the caregiver is at the patient support apparatus, the maintenance-event subroutine 222 proceeds to the decision step 267.

Decision step 267 determines whether the caregiver is authorized to give permission. If the caregiver is authorized, the maintenance-event subroutine 222 proceeds to a decision step 270 which determines whether the caregiver gives permission. If the caregiver is not authorized, the maintenance-event subroutine 222 returns to the decision step 260 to determine whether permission is required for action and another caregiver can respond. If the caregiver is authorized, then the maintenance-event subroutine 222 proceeds to the decision step 270 which determines whether the caregiver has authorized the predetermined action of the patient support apparatus 10 as shown in FIG. 7A.

If the caregiver gives permission, the maintenance-event subroutine 222 proceeds to take action in the process step 262 as suggested in FIG. 7A. During the process step 262, the control system 16 commands the patient support apparatus to implement the predetermined action. Next, the maintenance-event subroutine 222 proceeds to a decision step 272 which determines whether the predetermined action should be logged. If the action should be logged, the maintenance-event subroutine 222 proceeds to the logging subroutine 208 and then returns to the process step 202 of the process 200 in which the patient support apparatus 10 is powered on. If the action should not be logged, the maintenance-event subroutine 222 then returns to the process step 202 of the process 200 in which the patient support apparatus 10 is powered on.

Decision step 238 determines whether the caregiver has authorized the predetermined action of the patient support apparatus 10 as shown in FIG. 6A. In one example, the caregiver may provide authorization by interacting with a user interface on the patient support apparatus, a computer terminal, or a mobile device. If the caregiver provides authorization, the maintenance-event subroutine 222 proceeds to the process step 228 which causes the patient support apparatus 10 to take the predetermined action. Once the predetermined action occurs, the maintenance-event subroutine 222 proceeds to a decision step 240 that determines if the predetermined action should be logged as shown in FIG. 6B. If the caregiver does not provide authorization for the predetermined action, the maintenance-event subroutine 222 proceeds to a decision step 242 which determines if the caregiver would like to make an adjustment to the predetermined action as show in FIG. 6B.

If permission is not given by the caregiver at decision step 270, the maintenance-event subroutine 222 then proceeds to a decision step 274 as shown in FIGS. 7A and 7B. The decision step 274 of the maintenance-event subroutine 222 determines whether the caregiver desires to make an adjustment to the predetermined action of the patient support apparatus 10. If the caregiver desires to make an adjustment, the maintenance-event subroutine 222 proceeds to a process step 276 in which the caregiver makes the adjustment. The maintenance-event subroutine 222 then proceeds to a subsequent process step 278 in which the patient support apparatus 10 performs the adjusted action.

In the instance where the caregiver does not desire to make an adjustment, the maintenance-event subroutine 222 proceeds to a determination step 280 as shown in FIG. 7B. The determination step 280 determines whether the event should be canceled. If the caregiver cancels the event, the process proceeds to a process step 282 which cancels the event. The maintenance-event subroutine 222 then returns back to the process step 202 of the process 200 where the patient support apparatus 12 is powered on. If the caregiver does not desire to cancel event, the maintenance-event subroutine 222 proceeds to a decision step 284 which determines if a reminder should be provided. If a reminder should be provided, the maintenance-event subroutine 222 proceeds to a process step 286 which waits a predetermined time period before advancing back to decision step 274 which determines whether the caregiver desires to make an adjustment. If no reminder is desired, then the maintenance-event subroutine 222 proceeds to the process step 282 as illustrated in FIG. 7B.

After the maintenance-event subroutine 222 has performed the process step 278, the maintenance-event subroutine 222 proceeds to a decision step 288 which determines whether performing the actions should be logged as shown in FIG. 7B. If the event should be logged, the maintenance-event subroutine 222 proceeds to the logging subroutine 208 where the action is logged in memory 68 of the control system 16 or communicate the log to the hospital information system 18. If the event should not be logged, the maintenance-event subroutine 222 proceeds to the process step 202 in which the patient support apparatus 10 is powered on.

As shown in FIGS. 7A and 7C, the decision step 256 may determine that the action is not a predictive maintenance action, but instead a component failure action. When a component failure action is determined, the maintenance-event subroutine 222 proceeds to the decision step 258. The decision step 258 then determines if the event is a component failure event as shown in FIG. 7C. If the event is not a component failure event, the maintenance-event subroutine 222 proceeds to a process step 290 that communicates the event to caregiver. The maintenance-event subroutine 222 then proceeds monitors a caregiver action in a process step 292. After the caregiver takes action, the maintenance-event subroutine 222 proceeds to a determination step 294 that determines if the caregiver action should be logged.

When the event is determined to be a component failure in decision step 258, the maintenance-event subroutine 222 then proceeds to a decision step 296 as shown in FIG. 7C. Decision step 296 determines whether the patient support apparatus 10 requires permission from a caregiver to take an action. If the patient support apparatus 10 does not require permission from the caregiver, the maintenance-event subroutine 222 proceeds to a process step 298 in which a predetermined action occurs. In one illustrative example, sensor 60 detects that the heater 58 has failed. The processor 70 then looks in memory 68 to determine if a predetermined action may be taken without caregiver permission. In the illustrative example, the processor 70 may determine that stopping cooler 56 may be done without caregiver permission so that the patient is not over cooled.

If the patient support apparatus 10 does require permission, the maintenance-event subroutine 222 proceeds a subsequent decision step 300 which determines whether permission may be given remotely from the patient support apparatus 10. If the permission may be given remotely, the maintenance-event subroutine 222 proceeds a process step 302 which requests permission remotely from the caregiver. After notifying the caregiver, the maintenance-event subroutine 222 then proceeds to a decision step 304. If permission may not be given remotely, the maintenance-event subroutine 222 then proceeds to a process step 306 which summons the caregiver to the patient support apparatus 10. Once the caregiver is at the patient support apparatus, the maintenance-event subroutine 222 proceeds to decision step 304.

Decision step 304 determines whether the caregiver is authorized to give permission. If the caregiver is authorized, the maintenance-event subroutine 222 proceeds to a decision step 307 which determines whether the caregiver gives permission. If the caregiver is not authorized, the maintenance-event subroutine 222 returns to the decision step 296 to determine whether permission is required for action and another caregiver can respond. If the caregiver is authorized, then the maintenance-event subroutine 222 proceeds to the decision step 307 which determines whether the caregiver has authorized the predetermined action of the patient support apparatus 10 as shown in FIG. 7C.

Decision step 307 determines whether the caregiver has authorized the predetermined action of the patient support apparatus 10 as shown in FIG. 7C. If the caregiver provides authorization, the maintenance-event subroutine 222 proceeds to the process step 298 which causes the patient support apparatus 10 to take the predetermined action. Once the predetermined action occurs, the maintenance-event subroutine 222 proceeds to the determination step 294 that determines if the predetermined action should be logged as shown in FIG. 7C. If the caregiver does not provide authorization for the predetermined action, the maintenance-event subroutine 222 proceeds to a decision step 308 which determines if the caregiver would like to make an adjustment to the predetermined action as show in FIG. 7D.

The decision step 308 of the maintenance-event subroutine 222 determines whether the caregiver desires to make an adjustment to the predetermined action of the patient support apparatus 10. If the caregiver desires to make an adjustment, the maintenance-event subroutine 222 proceeds to a process step 310 in which the caregiver makes the adjustment. The maintenance-event subroutine 222 then proceeds to a decision step 312 which determines whether the adjusted action proposed by the caregiver should be reviewed by one of a supervisor, doctor, or the service provider 20.

In the instance where the caregiver does not desire to make an adjustment, the maintenance-event subroutine 222 proceeds to a determination step 314 as shown in FIG. 7D. The determination step 314 determines whether the event should be canceled. If the caregiver cancels the event, the maintenance-event subroutine 222 proceeds to a process step 316 which cancels the event. The maintenance-event subroutine 222 then returns back to the process step 202 of the process 200 where the patient support apparatus is powered on. If the caregiver does not desire to cancel event, the maintenance-event subroutine 222 proceeds to a decision step 318 which determines if a reminder should be provided. If a reminder should be provided, the maintenance-event subroutine 222 proceeds to a process step 320 which waits a predetermined time period before advancing back to the decision step 308 which determines whether the caregiver desires to make an adjustment. If no reminder is desired, then the maintenance-event subroutine 222 proceeds to the process step 316 as illustrated in FIG. 7D.

As described above, the maintenance-event subroutine 222, after caregiver makes an adjustment to the predetermined response in process step 310, advances to decision step 312 as shown in FIG. 7D. Decision step 312 determines if review of the adjustment is needed. In an example, the sensor 60 may be a position sensor that has detected the failure of one of several actuators responsible for moving the upper frame 24 relative to the lower frame 22. As a result, the control system 16 may determine that it should block future requests to move the upper frame 24 relative to the lower frame 22. However, during review by the caregiver, the caregiver may determine that the need for movement of the upper frame 24 relative to the lower frame is necessary for patient health. As a result, the caregiver adjusts the predetermined action so that movement of the upper frame 24 relative to the lower frame 22 is possible but at a slower rate of movement. The control system 16 then looks up in memory 68 whether such an adjustment is permissible and determines if the caregiver's adjustment should be reviewed in decision step 312.

If no review of the caregiver's adjustment is necessary, the maintenance-event subroutine 222 proceeds to process step 322 in which the adjusted action is performed by the patient support apparatus 10. If review is necessary, the maintenance-event subroutine 222 proceeds to the process step 324 and communicates the request for review to the appropriate party (supervisor, doctor, maintenance technician, or service provider). The maintenance-event subroutine 222 then proceeds to a decision step 326 in which the reviewing party determines whether the proposed adjusted action is acceptable. In the example of the broken actuator, the service provider may determine that movement of the upper frame 24 relative to the lower frame 22 using a limited number of actuators is unsafe and thus should not be allowed.

If the proposed adjustment is acceptable, the maintenance-event subroutine 222 proceeds to the process step 322 and then returns to the process step 202 of the process 200 in which the patient support apparatus 10 is powered on. If the proposed adjustment is not acceptable, the maintenance-event subroutine 222 proceeds to a subsequent decision step 328 which determines whether the adjusted action should be revised. If the proposed action should not be revised, then the maintenance-event subroutine 222 proceeds to a process step 330 that communicates to the caregiver the proposed adjusted action is not acceptable. The maintenance-event subroutine 222 then returns back to decision step 308 which determines if the caregiver wants to make an adjustment to the action.

Decision step 328 determines whether the reviewing party wishes to revise the adjusted action as shown in FIG. 7E. In the event the reviewing party does wish to revise the adjusted action, the maintenance-event subroutine 222 proceeds to a process step 330 in which the reviewing party provides the revised action. The maintenance-event subroutine 222 then proceeds to a subsequent process step 332 in which the revised action is communicated to the caregiver. Next, the maintenance-event subroutine 222 proceeds to a decision step 334 in which the caregiver determines whether to accept the revised action as shown in FIG. 7E. If the caregiver does not accept the revised action, the maintenance-event subroutine 222 returns to the process step 310 in which the caregiver inputs a new adjusted action. If the caregiver does accept the revised action, the maintenance-event subroutine 222 proceeds to a process step 336 in which the patient support apparatus 10 performs the revised action.

After the maintenance-event subroutine 222 has performed the process step 336, the maintenance-event subroutine 222 proceeds to a decision step 338 which determines whether performing the actions should be logged as shown in FIG. 7E. If the event should be logged, the maintenance-event subroutine 222 proceeds to the logging subroutine 208 where the action is logged in memory 68 of the control system 16 or communicate the log to the hospital information system 18. If the event should not be logged, the maintenance-event subroutine 222 proceeds to the process step 202 of the process 200 in which the patient support apparatus 10 is powered on.

Figure 8A:
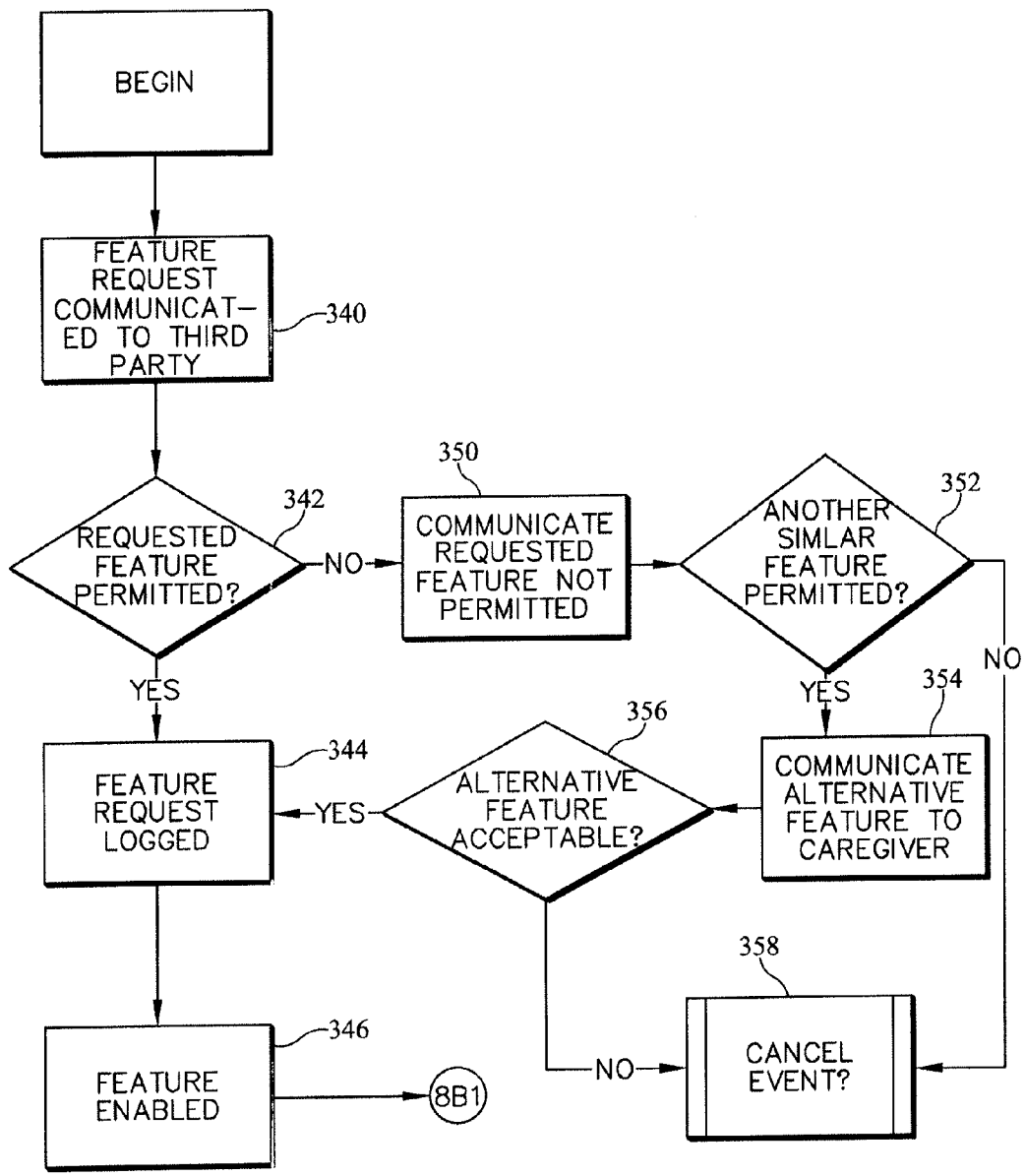
FIGS. 8A-8C are a series of flow charts showing a sub-routine related to feature-request events included in the control routine of FIG. 4.
Figure 8B:
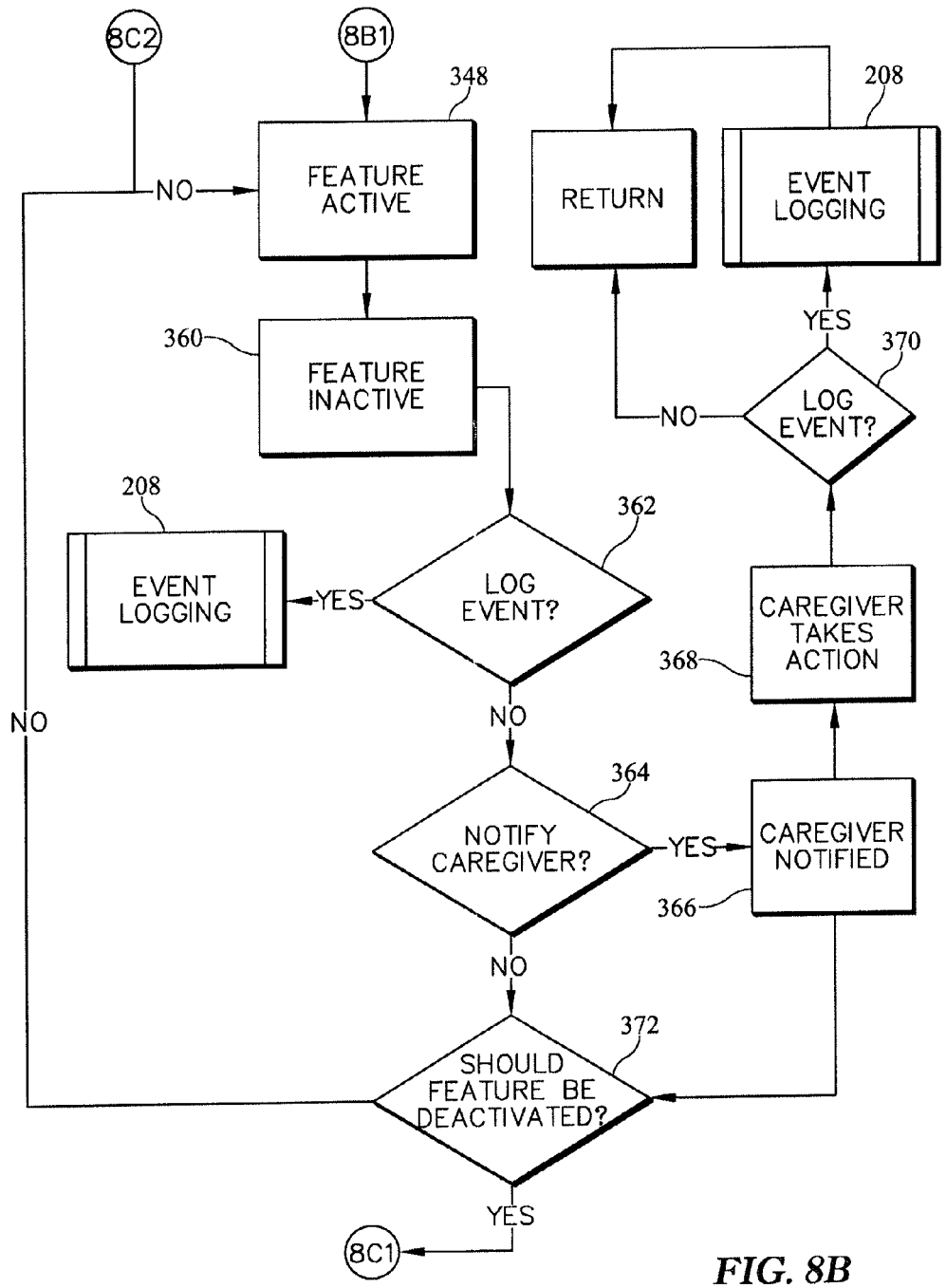
Figure 8C:
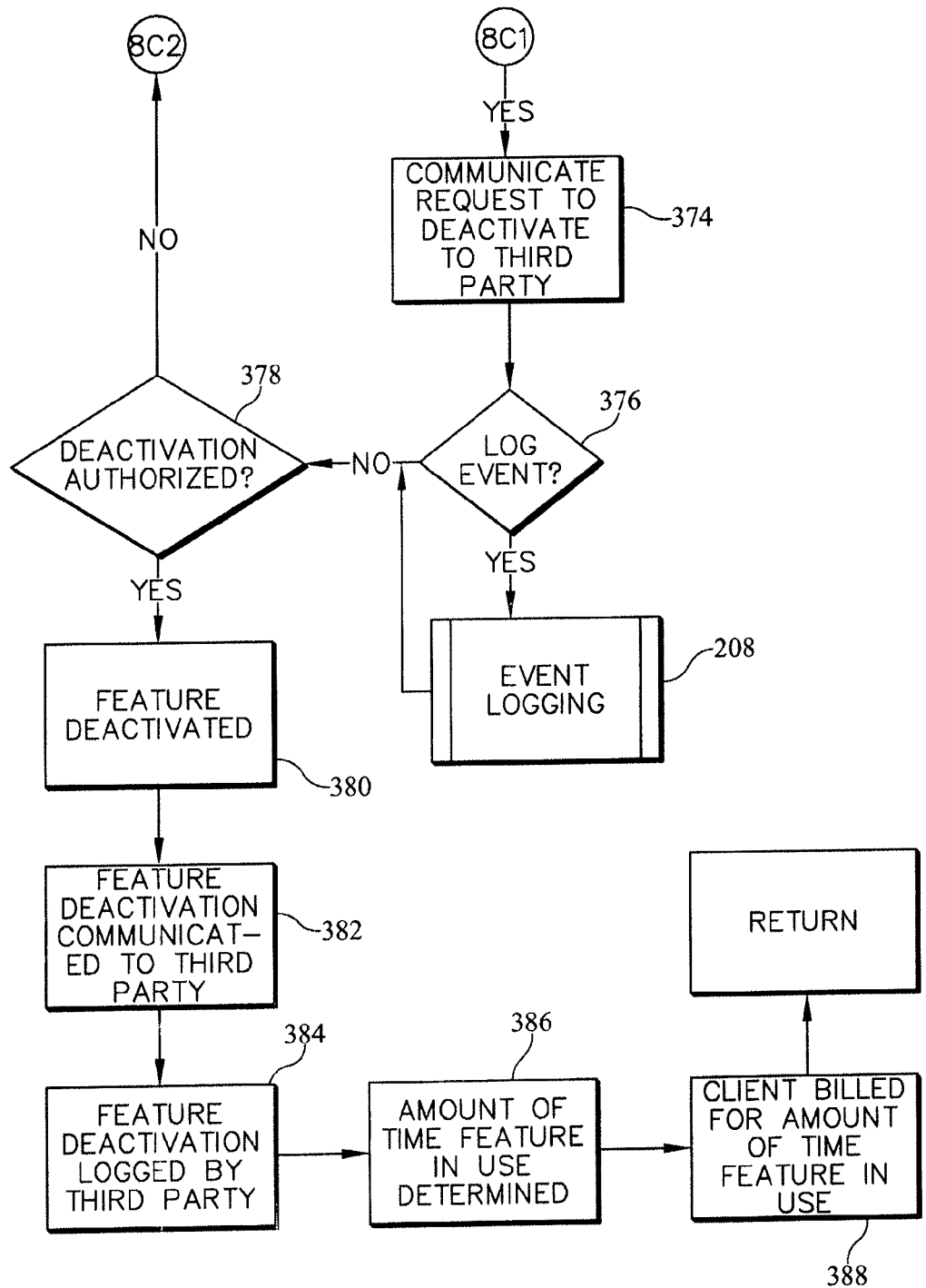

When the control system 16 determines that the event is a feature-request event in decision step 214, the process 200 then proceeds to the feature-request subroutine 224 as suggested in FIG. 4 and shown in detail in FIGS. 8A-8C. The feature-request subroutine 224 begins with a process step 340 in which the feature request is communicated to the service provider 20. The feature-request subroutine 224 then proceeds to a decision step 342 which determines if the requested feature is permitted as shown in FIG. 8A. Control system 16, computers at the service provider 20, or a user at the service provider will determine if the requested feature should be permitted. In one illustrative example, the patient support surface 14 may be configured to support the patient and the caregiver may determine that the patient is at risk for pressure ulcers and therefore makes a feature request. In this example, the feature requested may be a microclimate management system for the patient support surface 14.

In decision step 342, the control system 16 may look in memory 68 or communicate with the service provider 20 to determine if the requested feature should be enabled. In one example, the requested feature may not be enabled because the hardware comprising the patient support surface 14 is not capable of providing the requested feature. In another example, the requested feature may not be enabled because a doctor has determined such a feature is not beneficial to the patient. In still yet another example, the requested feature may not be enabled because the patient's insurance will not reimburse for use of the requested feature.

If the requested feature is permitted in decision step 342, the feature-request subroutine 224 proceeds to a process step 344 in which the feature request is logged in one or more of memory 68, memory included in computer on the hospital information system 18, and the service provider 20. The feature-request subroutine 224 then proceeds to a subsequent process step 346 in which the requested feature is enabled as suggested in FIG. 8A. The feature-request subroutine 224 continues to activate the feature in a process step 348 as shown in FIG. 8B.

If the requested feature is not permitted in decision step 342, the feature-request subroutine 224 proceeds to a process step 350 in which the communication is provided to the caregiver that the requested feature is not permitted. The feature-request subroutine 224 proceeds to a subsequent decision step 352 which determines if another similar feature is permitted. In one illustrative example, the caregiver may request the use of a microclimate management system for the patient support surface 14. The service provider may determine that the requested bed feature will not be reimbursed for by the patient's insurance provider. As a result, the service provider may offer a feature such as passing air through the patient support surface 14 to minimize sweating of the patient without the effort, expense, and time required to get the microclimate management system approved by the insurance provider or added the patient support apparatus 10.

If another similar feature is permitted, the feature-request subroutine 224 then communicates the alternative feature to the caregiver in a process step 354 as shown in FIG. 8A. The process then continues to a decision step 356 which determines if the alternative feature is acceptable. If the alternative feature is acceptable, the feature-request subroutine 224 proceeds to the process step 344 in which the feature request is logged. If the alternative is not acceptable, the feature-request subroutine 224 proceeds to a cancel-event subroutine 358 that determines whether to cancel the feature-request event.

After the process step 348 activates the requested feature, the feature-request subroutine 224 proceeds until a process step 360 occurs as suggested in FIG. 8B. The process step 360 is the deactivation of the feature or a request to deactivate the feature. As an example, the patient may attempt to deactivate one or more bed features such as an out-of-bed alarm. Once the feature is deactivated, the feature-request subroutine 224 proceeds to a determination step 362 that determines if the deactivation of the feature should be logged. If the deactivation of the feature should be logged, the feature-request subroutine 224 proceeds to the logging subroutine 208 and continues to a decision step 364. If the deactivation of the feature should not be logged, the feature-request subroutine 224 proceeds to the decision step 364 that determines if the caregiver should be notified of the feature deactivation.

The decision step 364 determines if the caregiver should be notified of the feature deactivation as shown in FIG. 8B. As an example, the deactivated feature may be the bed-exit alarm. The control system 16 would look up this feature in memory 68 or communicate with the hospital information system 18 or service provider 20 to determine if the bed-exit alarm should be deactivated. If the caregiver should be notified of the feature deactivation, the feature-request subroutine 224 proceeds to a process step 366 that notifies the caregiver the feature is now deactivated. The feature-request subroutine 224 then proceeds to allow the caregiver to take appropriate action in a process step 368. In one example, the caregiver may reactivate the bed-exit alarm. The feature-request subroutine 224 then continues to the logging subroutine 208 before continuing back to process step 202 in which the patient support apparatus is powered on.

After the process step 368, the feature-request subroutine 224 proceeds to a decision step 370 which determines whether the caregiver action should be logged. If the action should be logged, the feature-request subroutine 224 proceeds to the logging subroutine 208 before returning to the process step 202 of the process 200. If the action should not be logged, the feature-request subroutine 224 returns to the process step 202 of the process 200.

In the event the caregiver should not be notified, the feature-request subroutine 224 proceeds to a decision step 372 which determines if the feature should have been deactivated as shown in FIGS. 8B and 8C. If the feature should not have been deactivated, the feature-request subroutine 224 returns to process step 348 and activates the feature. If the feature should be deactivated, the feature-request subroutine 224 proceeds to process step 374 in which a request to deactivate the feature is communicated to one of the caregiver, the hospital, or the service provider 20. The feature-request subroutine 224 then proceeds to a determination step 376 which determines whether the deactivation request should be logged. If the request should be logged, the feature-request subroutine 224 proceeds to the logging subroutine 208 and then onto a decision step 378. If the request should not be logged, the feature-request subroutine 224 proceeds to the decision step 378.

The decision step 378 determines if the deactivation of the feature is authorized. If the feature deactivation is not authorized, the feature-request subroutine 224 returns to process step 348 which is the activation of the requested feature. If the feature deactivation is authorized, the feature-request subroutine 224 proceeds to deactivate the feature in a process step 380 as shown in FIG. 8C. The feature-request subroutine 224 then proceeds to a process step 382 in which the feature deactivation is communicated to at least one of the hospital information system 18 and the service provider 20. The feature-request subroutine 224 continues on to a subsequent process step 384 in which the feature deactivation is logged by at least one of the hospital information system 18 and the service provider 20. The feature-request subroutine 224 then proceeds to a process step 386 where the amount of time the feature was in use is calculated. Finally, the feature-request subroutine 224 continues to a process step 388 in which the client is billed for the amount of time the feature was in use. The client may be the hospital, the caregiver, the insurance company, or the patient as shown in FIG. 8C. The process then proceeds back to the process step 202 of the process 200 in which the patient support apparatus 10 is powered on.

Figure 5:
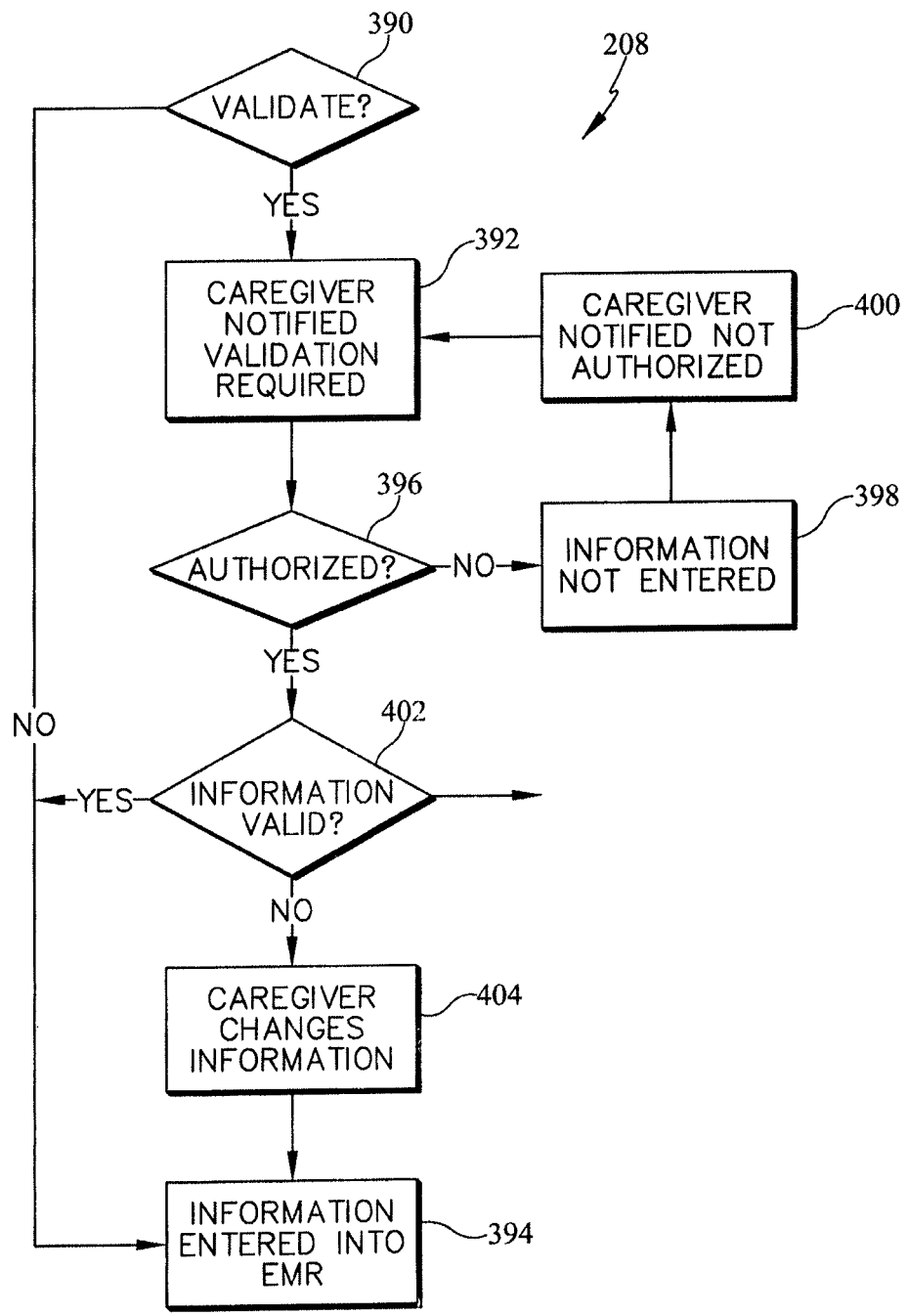
FIG. 5 is a flowchart of a sub-routine included in the control routine of FIG. 4.

As discussed above, the process 200, the patient-event subroutine 220, the maintenance-event subroutine 220, or the feature-request subroutine 224 may call on the logging subroutine 208 at various instances in process 200. The logging subroutine 208 begins with a decision step 390 that determines whether the event should be validated by a caregiver or other suitable person as shown in FIG. 5. If the event should be validated, the logging subroutine 208 proceeds to a process step 392 in which the caregiver is notified that validation is required. If the validation is not required, the logging subroutine 208 proceeds to a process step 394 in which the control system 16 enters the information into at least one of memory 68, the hospital information system 18, and a computer at the service provider 20.

Logging subroutine 208 then proceeds to a decision step 396 which determines if the caregiver is authorized to validate the information as shown in FIG. 5. If the caregiver is not authorized, the logging subroutine 208 then proceeds to a process step 398 in which the information is not logged. The logging subroutine 208 then proceeds to a subsequent process step 400 in which the caregiver is notified that the caregiver is not authorized to validate the information. The logging subroutine 208 then returns to process step 392 in which another caregiver is notified that validation is required.

If the caregiver is authorized to validate the information, the logging subroutine 208 proceeds to a decisions step 402 that determines if the information is valid and should be changed as suggested in FIG. 5. If the information is valid, the logging subroutine 208 proceeds to the process step 394 in which the information is logged. If the information is not valid, the logging subroutine 208 proceeds to a process step 404 in which the caregiver changes the information. The logging subroutine then continues on to the process step 394 in which the information is logged.

Figure 9:
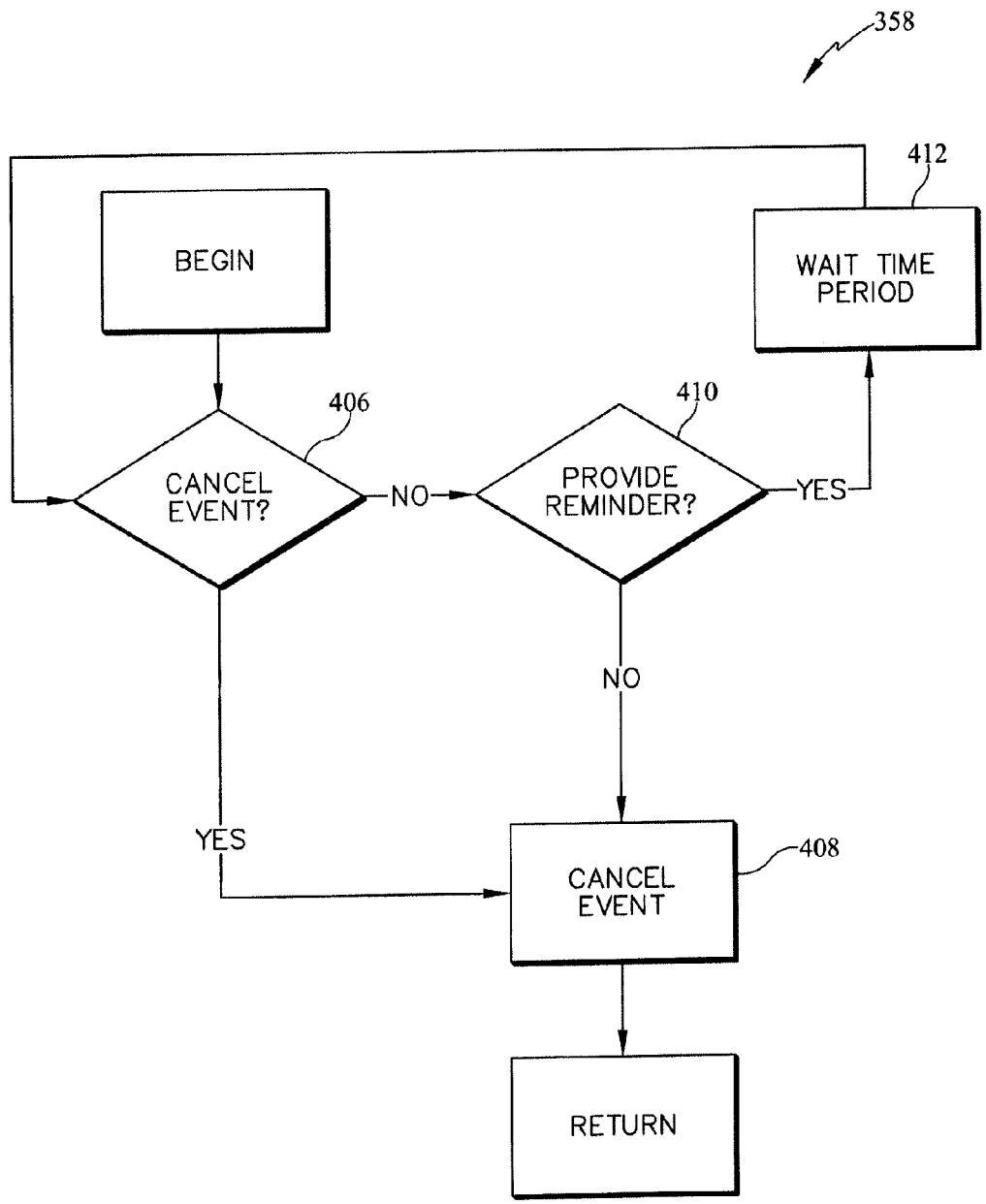
FIG. 9 is a flow chart of a sub-routine include in the sub-routine of FIG. 8A.

The process 200 also calls on the cancel-event subroutine 358 as shown in FIG. 8A and shown in more detail in FIG. 9. The cancel-event subroutine 358 begins with a decision step 406 that determines if the event should be canceled. If the event should be canceled, the cancel-event subroutine 358 proceeds to a process step 408 in which the event is canceled. The cancel-event subroutine then proceeds to return back to the process 200. If the event should not be canceled, the cancel-event subroutine 358 advances to a decision step 410 that determines if a reminder should be provided. If a reminder should be provided, the cancel-event subroutine 358 advances a process step 412 in which the cancel-event subroutine 358 waits a predetermined time period. Once the predetermined time period passes, the cancel-event subroutine 358 returns to the decision step 406 as shown in FIG. 9.

The process 200 is configured to respond once an event is detected by one or more sensors 60. Once the event is detected, the process 200 determines if the event is one of a patient event, a maintenance event, and a feature-request event. Depending on the event type, the process 200 takes appropriate action and returns to a state prior to the detection of an event. While several different patient events such as sweating, bed exit, and incontinence are mentioned, any other suitable patient events may be detected by and responded to by the control system 16. In addition, several different maintenance events such as a dirty filter, a broken actuator, and a malfunctioning fluid supply 36, any other suitable maintenance events may be detected by and responded to by the control system 16. Furthermore, several bed features such as air fluidized therapy 72, microclimate management 74, percussion therapy 76, vibration therapy 78, patient history and tracking 80, deep vain thrombosis therapy 82 are mentioned and shown in FIG. 3, any other requests for suitable features 84 may be detected and responded to by the control system 16.

Figure 10:
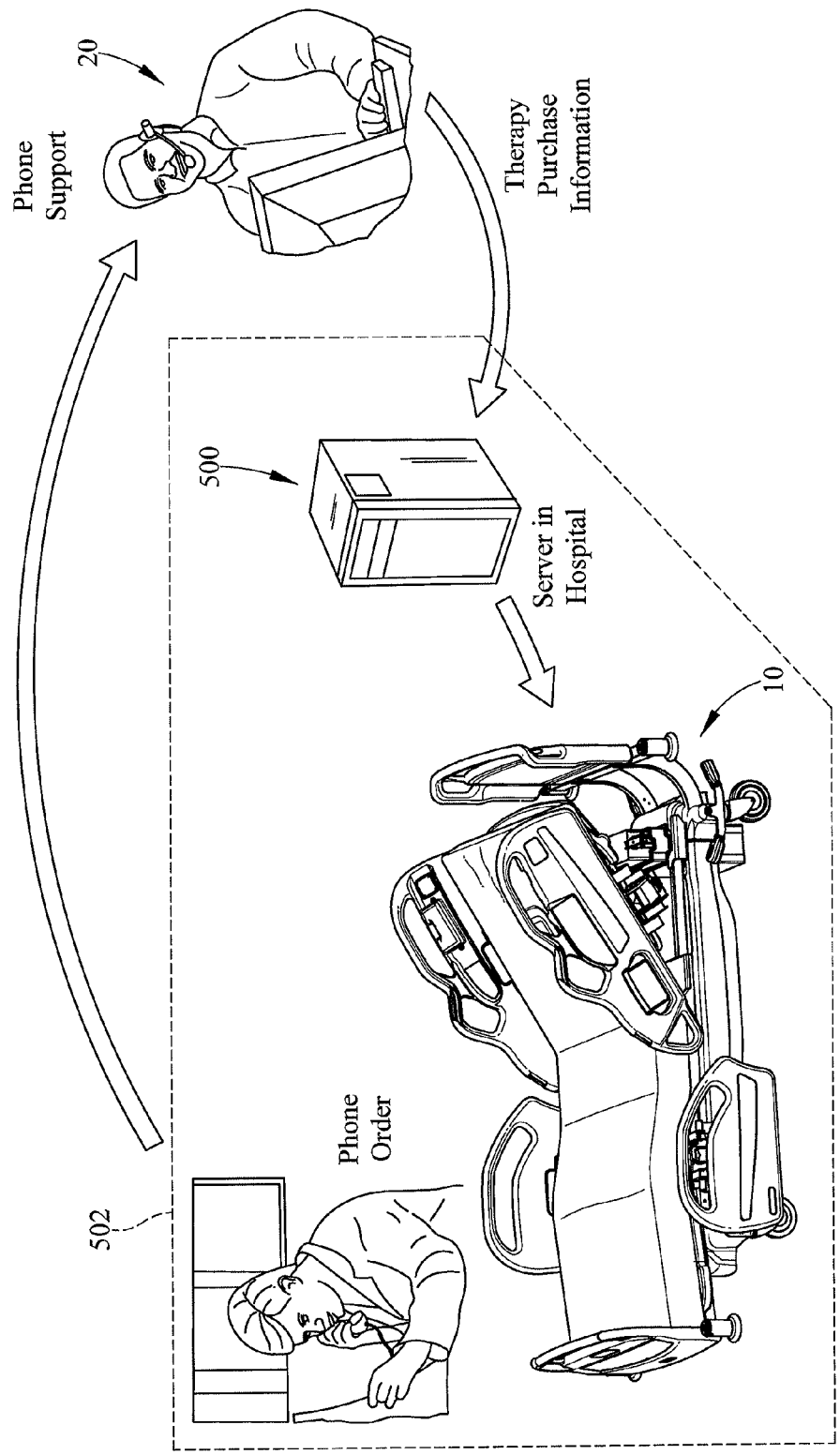
FIG. 10 is a diagrammatic representation of a first embodiment of a system that controls selectively enabled therapies on a patient support apparatus through an approval system that includes a service provider responding to a remote request from a caregiver.

Referring now to the embodiment of FIG. 10, the patient support apparatus 10 is equipped with hardware and software sufficient to allow it to communicate with information technology systems resident at a service provider 20 through a server 500 that is located in a hospital 502 and is accessed by the service provider 20 via the internet or telephone connection. In the embodiment of FIG. 10, the server 500 is dedicated to operation of all of the patient support apparatuses 10 in a particular hospital 502. In this embodiment, a caregiver may make a call to the service provider 20 requesting additional therapy availability on a particular patient support apparatus 10. The service provider 20 may engage the server 500 to enable the requested therapy on the particular patient support apparatus 10. In some cases, the server 500 may enable a number of distinct therapies on more than one patient support apparatus 10. For example, a wing, a floor, or some other grouping of patient support apparatuses 10 may all be simultaneously enabled.

In another embodiment shown in FIG. 11, a patient support apparatus 10 in a hospital 502 communicates with the server 500. A caregiver may request a therapy from the user interface on the patient support apparatus 10. The patient support apparatus 10 communicates with the server 500 to request activation of the therapy. The server 500 transmits the request to the service provider 20 and, upon approval of the therapy by the service provider 20, the service provider 20 transmits an authorization for the selected therapy to the server 500. The server 500 then enables the selected therapy on the specific patient support apparatus 10.

In still another embodiment shown in FIG. 12, the server 500 is connected to the hospital information system 18 and the service provider 20. An order for a therapy may be entered through the hospital information system 18 such as through an EMR or ERP terminal 504. The hospital information system 18, communicates the order for the therapy to the server 500. The server 500 transmits the request to the service provider 20 and, upon approval of the therapy by the service provider 20, the service provider 20 transmits an authorization for the selected therapy to the server 500. The server 500 then enables the selected therapy on the specific patient support apparatus 10. The enablement of the therapy may also be communicated to the hospital information system 18 to update the patient records.

In some embodiments, the system will aggregate all of the therapies enabled by the server 500 and consolidate a monthly bill for the hospital 502 from the service provider 20. The operation of the therapy or therapies may operate against a capitated amount, such as a total time or expense of therapy enablement for the hospital 502. The capitated amount may be a budgeted amount or a pre-authorized amount, such as by a purchase order to the service provider 20.

Although the invention has been described in detail with reference to certain illustrative embodiments, variations and modifications exist with the scope and spirit of this disclosure as described and defined in the following claims.

The invention claimed is:

1. A system comprising
a first patient support apparatus having at least one therapy device that is optionally and independently operational, the device being configured to be, when enabled for operation, capable of providing a distinct therapy to a patient supported on the patient support apparatus, the first patient support apparatus including (i) a control system operable to enable or disable operation of the therapy device under software control, and (ii) a user input device coupled to the control system, the user input device operational to receive a user input requesting enablement or disablement of the therapy device, wherein the control system is operable to communicate the request externally from the first patient support apparatus, and a server spaced apart from the first patient support apparatus, the server in communication with (a) the control system of the first patient support apparatus and (b) a computer device at a service provider, wherein the server is operable to receive the request for enablement or disablement of the therapy device from the control system of the first patient support apparatus, wherein the server is operable to transmit a received request for enablement or disablement of the therapy device to the computer device at the service provider, wherein the computer device is operable to process the request for enablement or disablement of the therapy device to determine whether the requested enablement or disablement of the therapy device is authorized, and to provide a signal to the server indicative of the permissibility of the request, wherein the server is operable to provide instructions to the control system to enable or disable the particular device of the first patient support apparatus, and wherein the server is operable to generate a bill for the enabled therapeutic device based the amount of time the therapeutic device is enabled.

2. The system of claim 1, wherein the server is in communication with a hospital information system, the hospital information system operational to receive a user input at a location remote from the first patient support apparatus requesting enablement or disablement of a particular therapy device of the first patient support apparatus and communicate the request to the server independently of the control system of the first patient support apparatus.

3. The system of claim 2, wherein the server is operable to transmit an authorization of the instructions to the control system to enable or disable the particular therapy device through the hospital information system.

4. The system of claim 1, wherein the computer device at the service provider is operable to monitor for an input from a user providing an indication that a particular therapy device of the first patient support apparatus is to be enabled or disabled, and to transmit an instruction to enable or disable the device to the server, and the server is operable to enable or disable the device based on the input from the user at the computer device at the service provider.

5. The system of claim 1, wherein the control system of the first patient support apparatus further includes a controller having a processor and a memory device, the processor in communication with the memory device, and a sensor in communication with the controller, the sensor operable to detect a parameter related to a patient supported on the first patient support apparatus or a status of a component of the first patient support apparatus, wherein the memory device includes instructions that, when executed by the processor, monitor a signal from the sensor and determine whether the signal from the sensor indicates that an event has occurred, and, if an event has occurred, add the occurrence to a record associated with the first patient support apparatus.

6. The system of claim 5, wherein the memory device includes further instructions that, when executed by the processor, determines whether the event is a patient event.

7. The system of claim 6, wherein the memory device includes further instructions that, when executed by the processor, determines whether caregiver interaction is required to respond to the patient event, and, if caregiver interaction is required, communicates with a caregiver to prompt interaction by the caregiver with the patient support apparatus.

8. The system of claim 7, wherein the memory device includes further instructions that, when executed by the processor, logs the event and the caregiver interaction.

9. The system of claim 7, wherein the memory device includes further instructions that, when executed by the processor, determines whether a non-patient event has occurred.

10. The system of claim 7, wherein the therapy device is configured to be optionally enabled to provide air fluidized therapy to a patient supported on the first patient support apparatus.

11. The system of claim 7, wherein the therapy device is configured to be optionally enabled to provide micro-climate management therapy to a patient supported on the first patient support apparatus.

12. The system of claim 7, wherein the therapy device is configured to be optionally enabled to provide percussion therapy to a patient supported on the first patient support apparatus.

13. The system of claim 7, wherein the therapy device is configured to be optionally enabled to provide deep vein thrombosis therapy to a patient supported on the first patient support apparatus.

14. The system of claim 1, wherein the therapy device is configured to be optionally enabled to provide air fluidized therapy to a patient supported on the first patient support apparatus.

15. The system of claim 1, wherein the therapy device is configured to be optionally enabled to provide micro-climate management therapy to a patient supported on the first patient support apparatus.

16. The system of claim 15, wherein the control system of the first patient support apparatus further includes a controller having a processor and a memory device, the processor in communication with the memory device, and a sensor in communication with the controller, the sensor operable to detect a parameter related to a patient supported on the first patient support apparatus or a status of a component of the first patient support apparatus, wherein the memory device includes instructions that, when executed by the processor, monitor a signal from the sensor and determine whether the signal from the sensor indicates that an event has occurred, and, if an event has occurred, add the occurrence to a record associated with the first patient support apparatus.

17. The system of claim 16, wherein the memory device includes further instructions that, when executed by the processor, determines whether the event is a patient event.

18. The system of claim 16, wherein the memory device includes further instructions that, when executed by the processor, determines whether caregiver interaction is required to respond to the event, and, if caregiver interaction is required, communicates with a caregiver to prompt interaction by the caregiver with the patient support apparatus.

19. The system of claim 1, wherein the therapy device is configured to be optionally enabled to provide percussion therapy to a patient supported on the first patient support apparatus.

20. The system of claim 1, wherein the therapy device is configured to be optionally enabled to provide deep vein thrombosis therapy to a patient supported on the first patient support apparatus.

* * * * *